(12) United States Patent
Bennet et al.

(10) Patent No.: US 10,791,974 B2
(45) Date of Patent: Oct. 6, 2020

(54) DIAMOND-CONTAINING ELECTRODES FOR NEUROCHEMICAL DETECTION

(71) Applicant: Mayo Foundation for Medical Education and Research, Rochester, MN (US)

(72) Inventors: Kevin E. Bennet, Rochester, MN (US); Kendall H. Lee, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 358 days.

(21) Appl. No.: 15/680,401

(22) Filed: Aug. 18, 2017

(65) Prior Publication Data

US 2018/0092575 A1 Apr. 5, 2018

Related U.S. Application Data

(60) Provisional application No. 62/377,411, filed on Aug. 19, 2016.

(51) Int. Cl.
| | |
|---|---|
| *A61B 5/05* | (2006.01) |
| *A61B 5/1473* | (2006.01) |
| *A61B 5/00* | (2006.01) |
| *A61N 1/36* | (2006.01) |
| *A61N 1/05* | (2006.01) |
| *G01N 33/50* | (2006.01) |
| *G01N 27/30* | (2006.01) |

(Continued)

(52) U.S. Cl.
CPC .......... *A61B 5/1473* (2013.01); *A61B 5/4064* (2013.01); *A61B 5/4836* (2013.01); *A61B 5/6868* (2013.01); *A61N 1/0534* (2013.01); *A61N 1/36121* (2013.01); *G01N 27/308* (2013.01); *G01N 33/4833* (2013.01); *G01N 33/50* (2013.01); *A61B 5/14546* (2013.01)

(58) Field of Classification Search
CPC ... A61B 5/1473; A61B 5/4836; A61B 5/4064; A61B 5/6868; A61B 5/14546; G01N 33/4833; G01N 27/308; G01N 33/50; A61N 1/0534; A61N 1/36121
See application file for complete search history.

(56) References Cited

U.S. PATENT DOCUMENTS

| | | | |
|---|---|---|---|
| 9,036,148 B2 | 5/2015 | Newton et al. | |
| 2005/0226774 A1* | 10/2005 | Kounaves | G01N 33/1846 422/80 |

(Continued)

OTHER PUBLICATIONS

Kurita et al. An sp2 and sp3 Hybrid Nanocrystalline Carbon Film Electrode for Anodic Stripping Voltammetry and Its Application for Electrochemical Immunoassay. Analytic Sciences. Jan. 2012. vol. 28 (Year: 2012).*

(Continued)

*Primary Examiner* — Christian Jang
(74) *Attorney, Agent, or Firm* — Fish & Richardson P.C.

(57) ABSTRACT

This document provides methods and materials involved in assessing concentrations of analytes in an environment using a diamond-containing carbon electrode. For example, methods and materials for using FSCV or paired pulse voltammetry to discriminate analytes based on their adsorption characteristics to a diamond-containing carbon electrode are described herein.

9 Claims, 16 Drawing Sheets

(51) Int. Cl.
 G01N 33/483 (2006.01)
 A61B 5/145 (2006.01)

(56) References Cited

U.S. PATENT DOCUMENTS

| 2006/0015024 A1* | 1/2006 | Brister | A61B 5/1411 600/345 |
| 2006/0293578 A1* | 12/2006 | Rennaker | A61B 5/0002 600/378 |
| 2013/0023745 A1 | 1/2013 | Lee et al. | |
| 2013/0123600 A1* | 5/2013 | Tcheng | A61B 5/0205 600/378 |

OTHER PUBLICATIONS

Ullah et al. Electrical conductivity enhancement by boron-doping in diamondusing first principle calculations. Applied Surface Science 334 (2015) 40-44. (Year: 2015).*
Agnesi et al., "Wireless Instantaneous Neurotransmitter Concentration System-based amperometric detection of dopamine, adenosine, and glutamate for imtraoperative neurochemical monitoring," *J. Neurosurg.*, 111(4):701-711, Oct. 2009.
Arumugam et al., "Characterization of ultrananocrystalline diamond microsensors for in vivo dopamine detection," *Appl Phys Lett.*, 102(25):253107, Jun. 24, 2013.
Bennet et al., "A diamond-based electrode for detection of neurochemicals in the human brain," *Methods.*, 10:Article 102, Mar. 15, 2016, 12 pages.
Bennet et al., "Development of Conductive Boron-Doped Diamond Electrode: A microscopic, Spectroscopic, and Voltammetric Study," *Materials.*, 6(12):5726-5741, Dec. 6, 2013.
Bernard et al., "About the origin of th elow wave number structures of the Raman spectra of heavily boron doped diamond films," *Diam Relat Mater.*, 13(4-8):896-899, 2004.
Bledsoe et al., "Development of the Wireless Instantaneous Neurotransmitter Concentration System for intraoperative neurochemical monitoring using fast-scan cyclic voltammetry," *J Neurosurg.*, 111(4):712-723, Oct. 2009.
Buckshire., "An overview of carbon fiber electrodes used in neurochemical monitoring," Thesis submitted to the University of Pittsburgh Graduate Faculty of Arts and Sciences., 2008, 40 pages.
Chang et al., "Wireless fast-scan cyclic voltammetry measurement of histamine using WINCS—a proof-of-principle study," *Analyst.*, 137(9):2158-2165, May 7, 2012.
Chang et al., "Wireless fast-scan cyclic voltammetry to monitor adenosine in patients with essential tremor during deep brain stimulation," *Mayo Clin Proc.*, 87(8):760-765, Aug. 2012.
Grahn et al., "A neurochemical closed-loop controller for deep brain stimulation: toward individualized smart neuromodulation therapies," *Front Neurosci.*, 8:169, Jun. 25, 2014.
Hudak., "Electrochemical evaluation of platinum and diamond electrodes for neural stimulation," Thesis submitted May 2011, Department of Chemical Engineering, Case Western Reserve University., 160 pages.
Kasasbeh et al., "Wireless neurochemical monitoring in humans," *Stereotact Funct Neurosurg.*, 91:141-147, 2013.
Kishida et al., "Sub-second dopamine detection in human striatum," *PloS one.*, 6(8):e23291, 2011, 5 pages.
Macpherson., "A practical guide to using boron doped diamond in electrochemical research," *Phys Chem Chem Phys.*, 17(5):2935-2949, Feb. 7, 2015.
Medel et al., "Surface activation of C-sp3 in boron-doped diamond electrode," *Electrocatalysis.*, 4:189-195, 2013.
Paek et al., "Neurotransmitter monitoring via boron-doped diamond electrode-based voltammetry during human deep brain stimulation in essential tremor," Presented Oct. 18, 2015, Poster, 3 pages.
Paek et al., "Dopamine measurement during prolonged deep brain stimulation. A proof-of-principle study of paired pulse voltammetry," Biomedical Engineering Lett., 3:22-31, 2013.
Robblee et al., "Electrical stimulation with Pt electrodes. V. The effect of protein on Pt dissolution," *Biomaterials.*, 1(3):135-139, Jul. 1980.
Robertson., "Diamond-like amorphous carbon," *Mater Sci Engin R.*, 37:129-281, 2002.
Robinson et al., "Detecting subsecond dopamine release with fast-scan cyclic voltammetry in vivo," *Clin Chem.*, 49(10):1763-1773, Oct. 2003.
Runnels et al., "Effect of pH and surface functionalities on the cyclic voltammetric responses of carbon-fiber microelectrodes," *Anal Chem.*, 71(14):2782-2789, 1999.
Sanchez-Gonzalez et al., "The primate thalamus is a key target for brain dopamine," *J Neurosci.*, 25(26):6076-6083, Jun. 29, 2005.
Shon et al., "Comonitoring of adenosine and dopamine using the Wireless Instantaneous Neurotransmitter Concentration System: proof of principle," *J Neurosurg.*, 112(3):539-548, Mar. 2010.
Swamy and Venton., "Subsecond detection of physiological adenosine concentrations using fast-scan cyclic voltammetry," *Anal Chem.*, 79(2):744-750, Jan. 5, 2007.
Takmakov et al., "Carbon Microelectrodes with a Renewable Surface," Analytical Chemistry., 82(5):2020-2028, Mar. 1, 2010.
Tomshine et al., "Development of boron-doped diamond microelectrodes for human use: electrode engineering and fabrication," Presented Oct. 17, 2015, Poster, 3 pages.
Yang et al., "Diamond electrochemistry at the nanoscale: A review," *Carbon.*, 99:90-110, 2016.

* cited by examiner

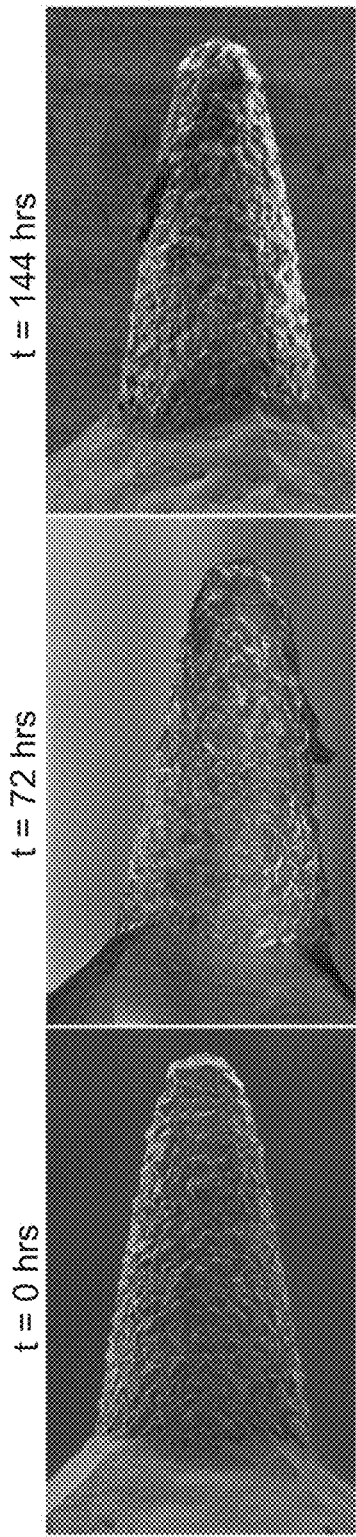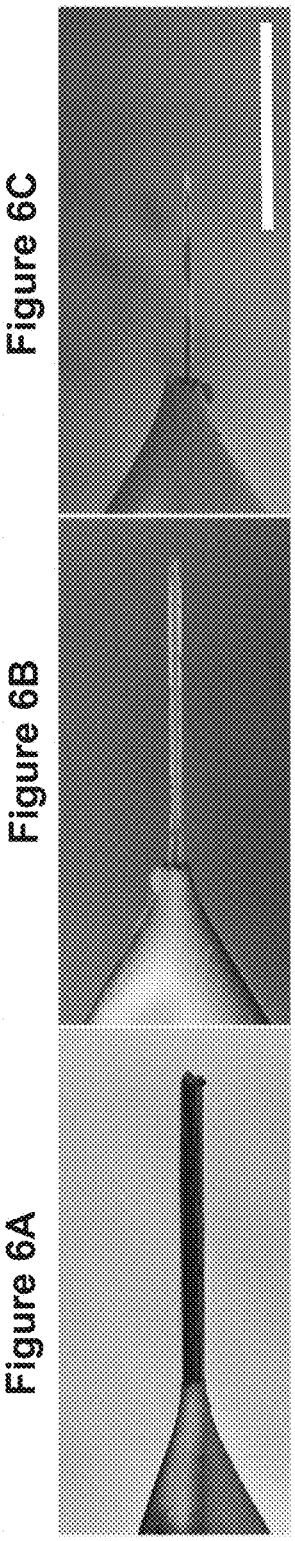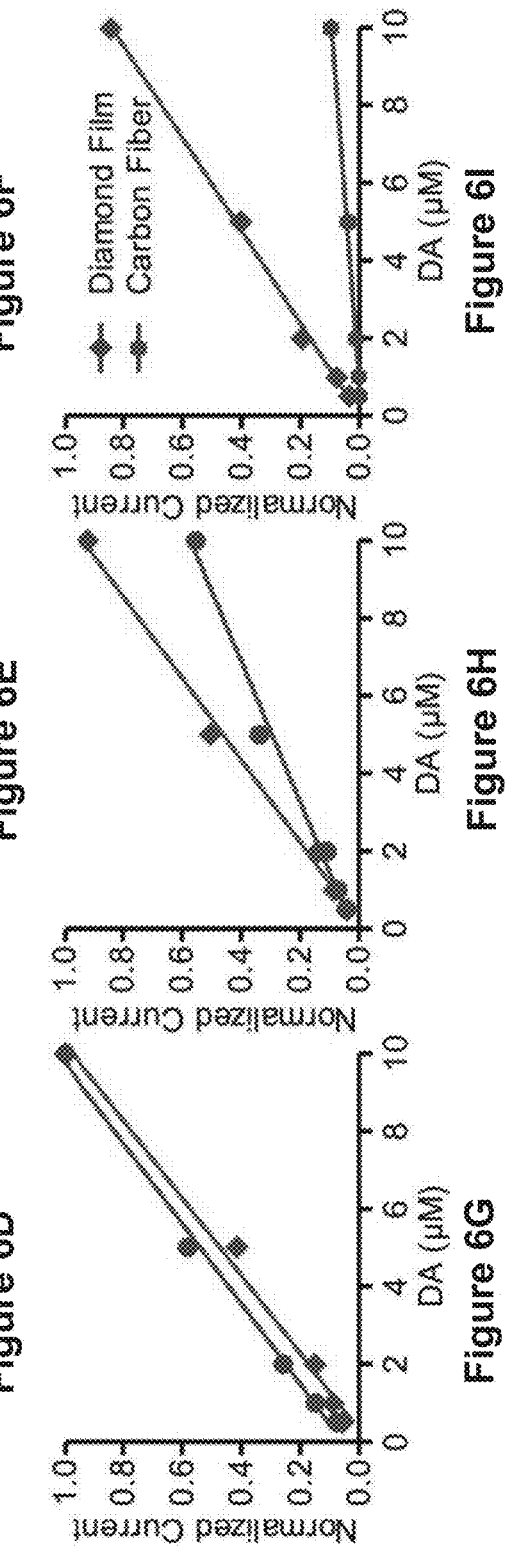

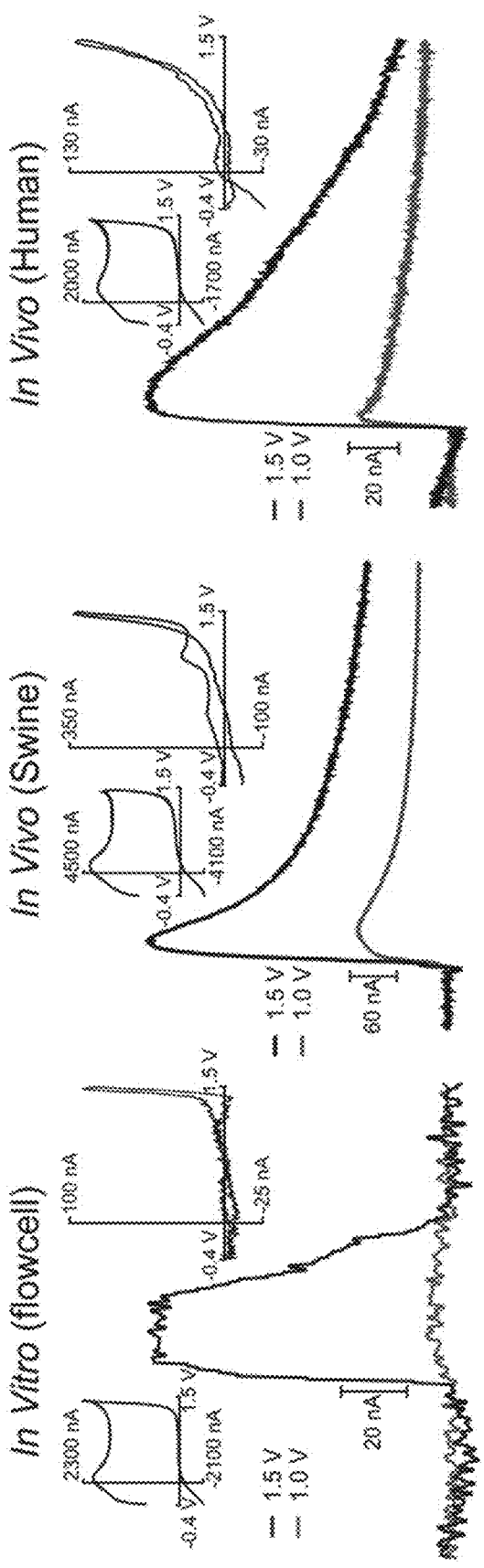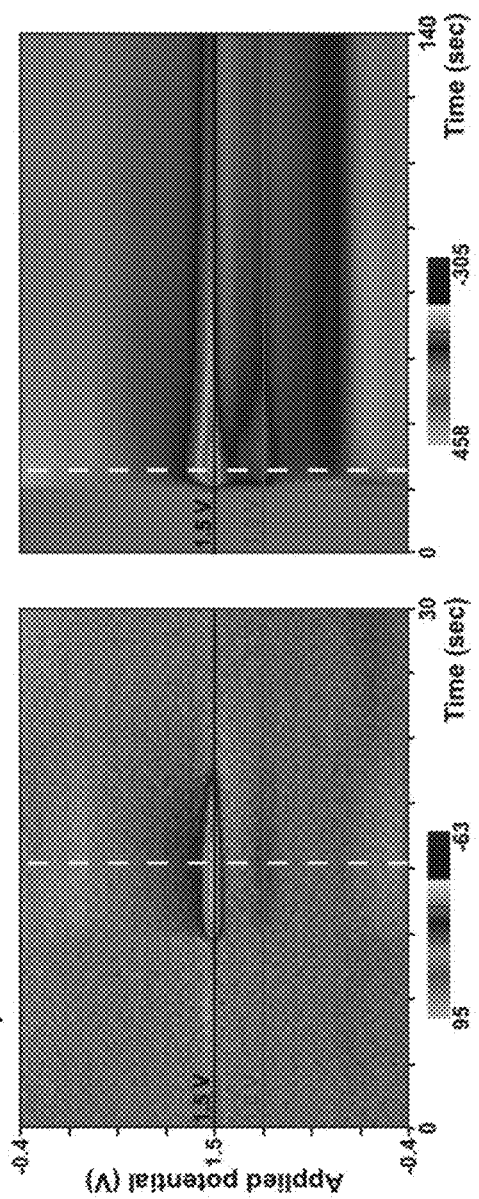
Figure 7A  Figure 7B  Figure 7C

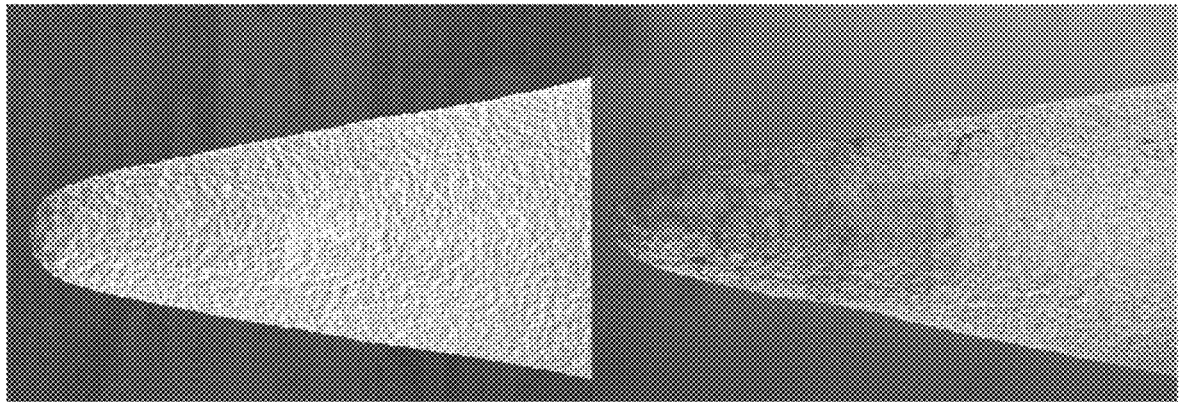
Figure 16A    Figure 16B
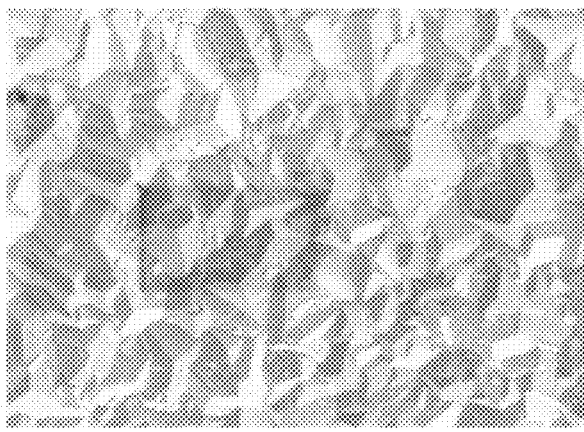  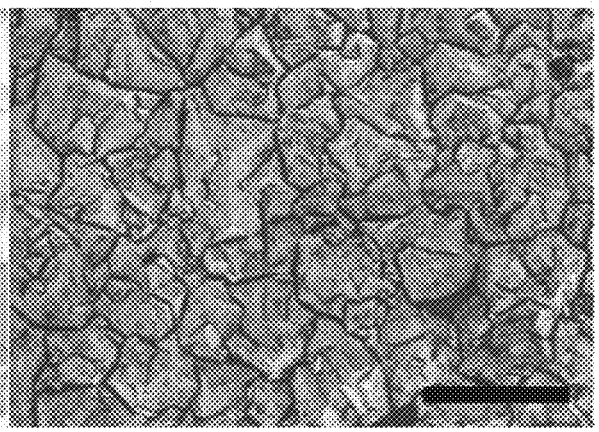
Figure 16C    Figure 16D

DIAMOND-CONTAINING ELECTRODES FOR NEUROCHEMICAL DETECTION

CROSS-REFERENCE TO RELATED APPLICATIONS

This application claims the benefit of U.S. Provisional Application Ser. No. 62/377,411, filed Aug. 19, 2016. The disclosure of the prior application is considered part of (and is incorporated by reference in) the disclosure of this application.

BACKGROUND

1. Technical Field

This document relates to methods and materials involved in differentiating analytes detected in an environment. For example, an electrode made of diamond-containing material may be used in performing voltammetry methods (e.g., paired pulse voltammetry, cyclic voltammetry) to discriminate analytes based on their adsorption characteristics to the electrode.

2. Background Information

Deep brain stimulation (DBS) is a surgical technique for treating certain neurologic and psychiatric conditions through the application of local stimulation to one or more areas of the brain. Some DBS systems utilize microprobes implanted in a patient for long-term, continuous monitoring of chemical activity in one or more areas of the brain. The microprobes may include one or more working electrodes that are capable of detecting the presence and level of various neurochemicals, such as dopamine and serotonin. Information about the detected neurochemicals can be transmitted to a controller that affects characteristics of the local stimulation, such as the frequency and amplitude of the stimulation. Some DBS systems employ carbon-fiber microelectrodes.

SUMMARY

This document generally provides methods and materials involved in detecting and assessing levels of neurochemicals in an environment using electrodes having sensors made of a diamond material.

In some implementations, the diamond-containing electrode can be used in a system that employs cyclic voltammetry (CV) to detect and discriminate among various neurochemicals or other analytes in an environment. CV is a type of potentiodynamic electrochemical measurement that can be used to evaluate the electrochemical properties of an analyte in solution. CV typically involves ramping the potential of a working electrode linearly versus time like linear sweep voltammetry. Unlike linear sweep voltammetry, which ends when it reaches a set potential, the working electrode's potential ramp in CV is inverted when it reaches a set potential. The inversion can happen multiple times during a single evaluation. The current at the working electrode can be plotted versus the applied voltage to give the cyclic voltammogram trace.

Implementations of the diamond-containing electrodes described herein can provide, in certain instances, various technical advantages including improved longevity, stability, and suitability for continuous monitoring and mechanical robustness.

Some implementations of the subject described herein include an electrode. The electrode can be configured to sense an analyte present within an environment. An outer surface of a sensing portion of the electrode can be made from a diamond-containing material that includes a composition of both $sp^3$-hybridized carbon and $sp^2$-hybridized carbon. In some implementations, a method can be performed that includes positioning the electrode in the environment, and performing a voltammetric technique using the electrode to sense a characteristic of the analyte in the environment.

Some implementations of the subject matter described herein include an apparatus for sensing an analyte present within an environment. The apparatus can include an electrical power source and a probe that is configured (i) to apply, using energy delivered from the electrical power source, an electrical stimulus to tissue of a mammal within the environment and (ii) to detect, within the environment, a response to the electrical stimulus that indicates a level of the analyte present within the environment. The probe can include an electrode for at least one of applying the electrical stimulus or detecting the response to the electrical stimulus, wherein the probe is made at least in part from a diamond-containing carbon material that includes a composition of both sp3-hybridized carbon and $sp^2$-hybridized carbon.

Some implementations of the subject matter described herein include a method of making an electrode for sensing an analyte present within an environment. The method can include providing a body of the electrode and coating a diamond-containing carbon material over at least a portion of the body of the electrode, wherein the diamond-containing carbon material includes a composition of both $sp^3$-hybridized carbon and $sp^2$-hybridized carbon.

Some implementations of the subject matter described herein include a method. The method can include locating a probe that includes a diamond-containing electrode according to any of the implementations described herein in a region of a brain of a mammal; generating, with the probe, an electrical stimulus and applying the electrical stimulus to brain tissue of the mammal; monitoring a response to the electrical stimulus that occurs in the region of the brain of the mammal, including sensing with the electrode a neurochemical or an ion in the region of the brain of the mammal that results from the electrical stimulus; and outputting (e.g., visually, haptically, and/or aurally presenting to a user) information about the level of the neurochemical or the ion in the region of the brain of the mammal that results from the electrical stimulus.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

Figure 4A:
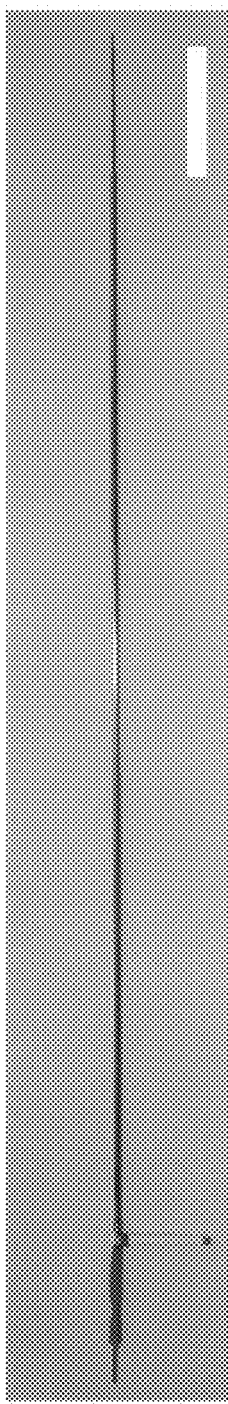
FIG. 4A is a first image of an example diamond-containing electrode.
Figure 4B:
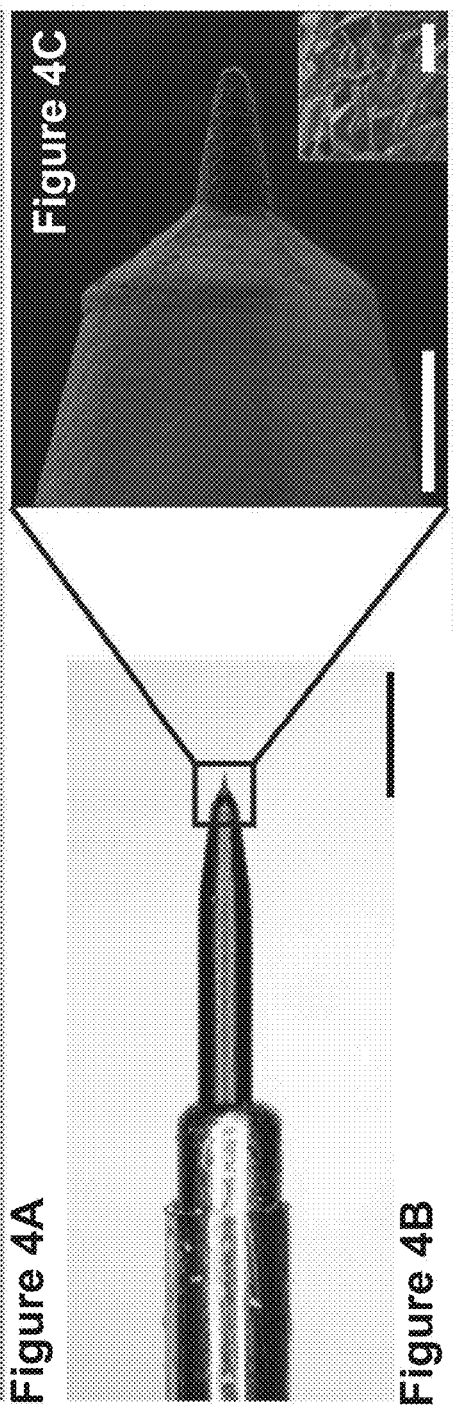
FIG. 4B is a second image of the electrode, focused on the tip of the electrode.
Figure 4C:
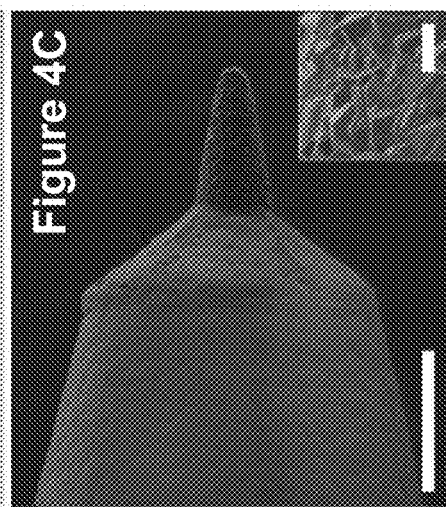
FIG. 4C is a third image of the electrode, further zoomed into the tip.
Figure 4F:
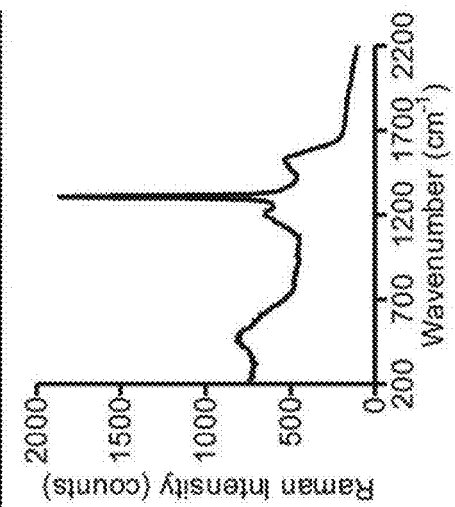
FIG. 4D is an image of a Raman microscopy of the electrode tip.
FIG. 4E is an additional image of a Raman microscopy of the electrode tip.

The integrated Raman spectrum is presented in FIG. 4F.

Figures 5A, 5B, 5C:
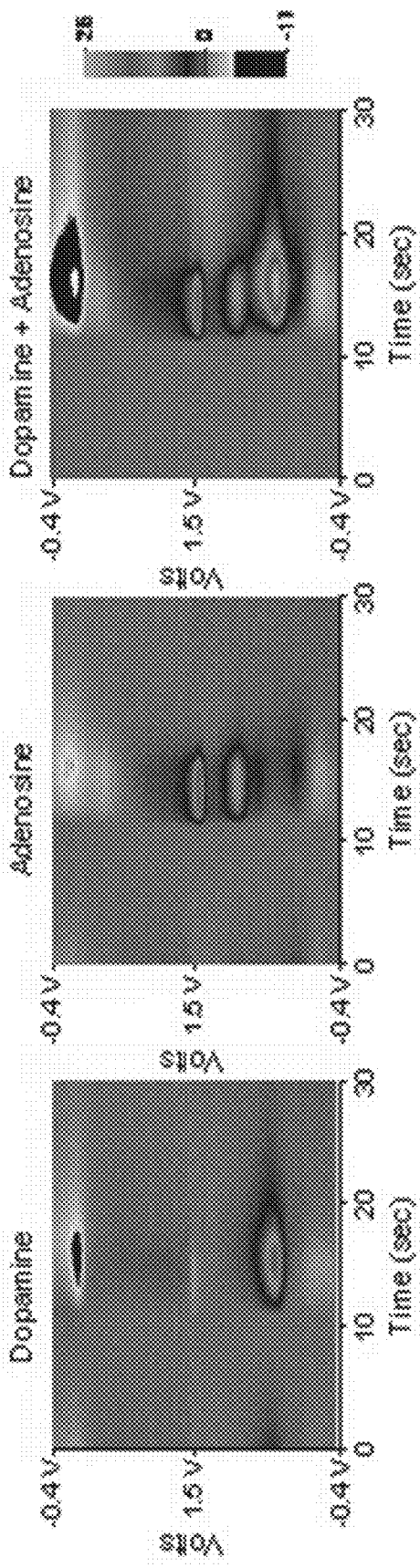

FIG. 5A is a plot of an oxidation and reduction signature of dopamine presented to a diamond-containing electrode in a flow cell.

FIG. 5B is a plot of an oxidation and reduction signature of adenosine presented to the electrode in a flow cell.

FIG. 5C is a plot of an oxidation and reduction signature of dopamine and adenosine presented to the electrode in a flow cell.

FIG. 6A is a first image of a scanning electron micrograph of a tip of a diamond-containing electrode.

FIG. 6B is a second image of a scanning electron micrograph of a tip of a diamond-containing electrode.

FIG. 6C is a third image of a scanning electron micrograph of a tip of a diamond-containing electrode.

FIG. 6D is a fourth image of a scanning electron micrograph of a tip of a diamond-containing electrode.

FIG. 6E is a fifth image of a scanning electron micrograph of a tip of a diamond-containing electrode.

FIG. 6F is a sixth image of a scanning electron micrograph of a tip of a diamond-containing electrode.

FIG. 6G is a first plot indicating empirical sensitivity of the electrode to dopamine in an experiment.

FIG. 6H is a second plot indicating empirical sensitivity of the electrode to dopamine in an experiment.

FIG. 6I is a third plot indicating empirical sensitivity of the electrode to dopamine in the experiment.

FIG. 7A shows plots representing results of inserting a diamond-containing electrode into a target therapy region in a flowcell, thereby stimulating release of the neurochemical adenosine due to the "microthalamotomy" effect.

FIG. 7B shows plots representing results of inserting the electrode in vivo in swine.

FIG. 7C shows plots representing results of inserting the electrode in vivo in a human.

Figures 8A, 8B:
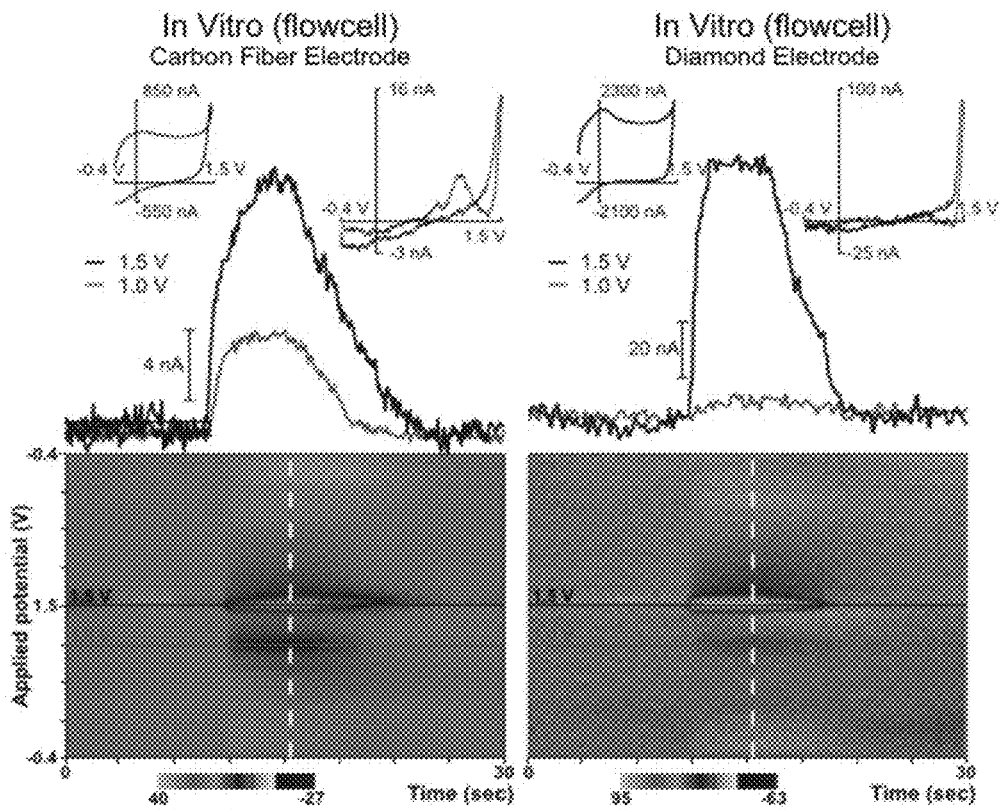

FIG. 8A depicts plots of a carbon fiber electrode inserted in vitro in a flowcell.

FIG. 8B depicts plots of a diamond electrode inserted in vitro in a flowcell.

Figures 8C, 8D:
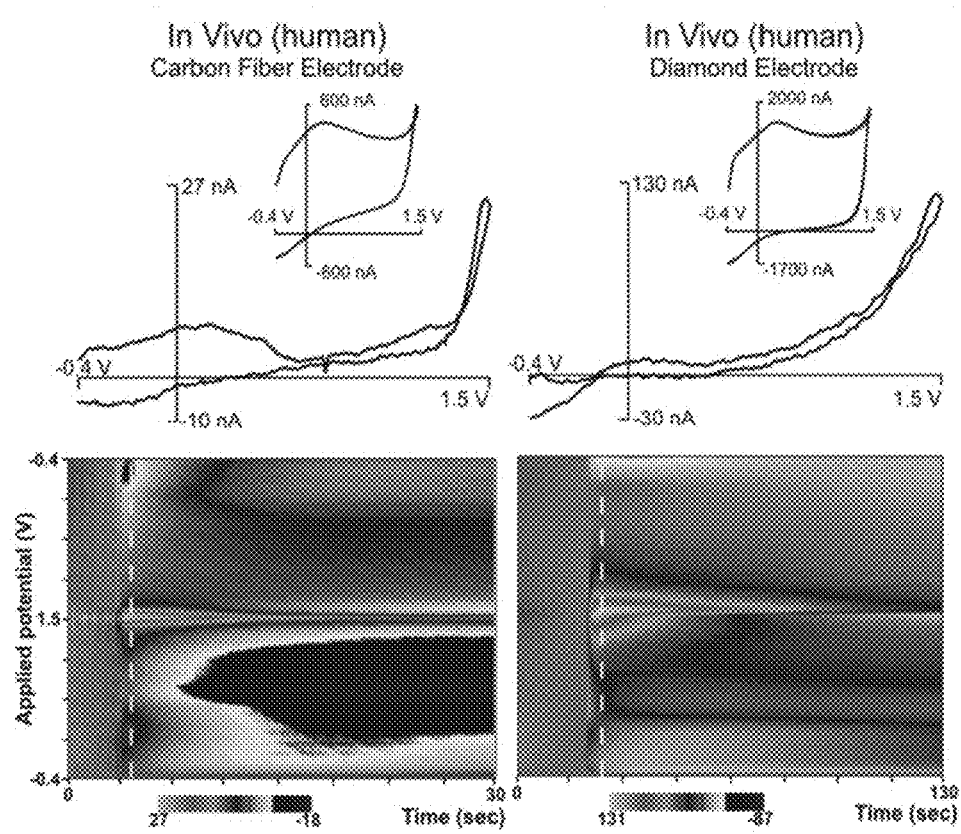

FIG. 8C depicts plots of a carbon fiber electrode inserted in vivo in a human.

FIG. 8D depicts plots of a diamond electrode inserted in vivo in a human. These results show adenosine-like signatures secondary to mechanical stimulation.

Figure 9A:
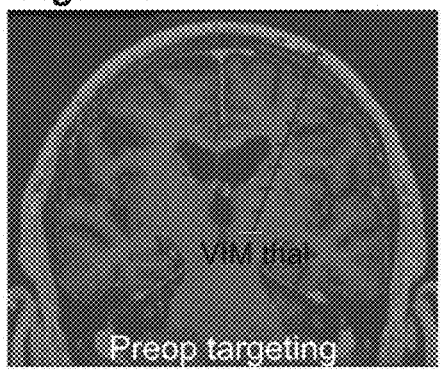

FIG. 9A depicts an image showing pre-op targeting for placement of a wireless instantaneous neurochemical concentration detection system (WINCS) and diamond-containing electrode for an example patient.

Figure 9B:
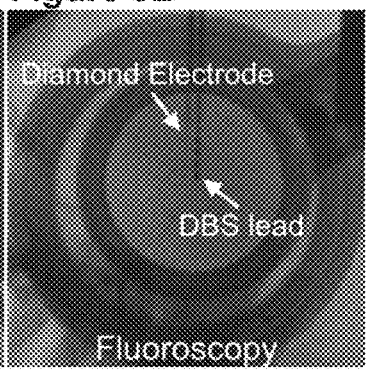

FIG. 9B is an image that depicts placement of the electrode in a brain of an individual.

Figure 9C:
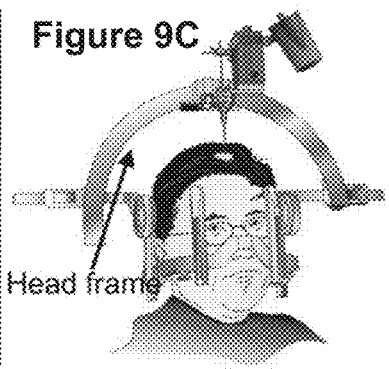

FIG. 9C is a representation of a system for placement of the electrode.

Figure 9D:
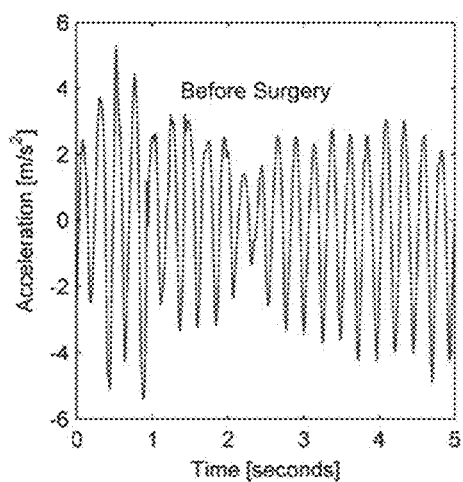

FIG. 9D shows a pre-operation tremor acceleration plot.

Figure 9E:
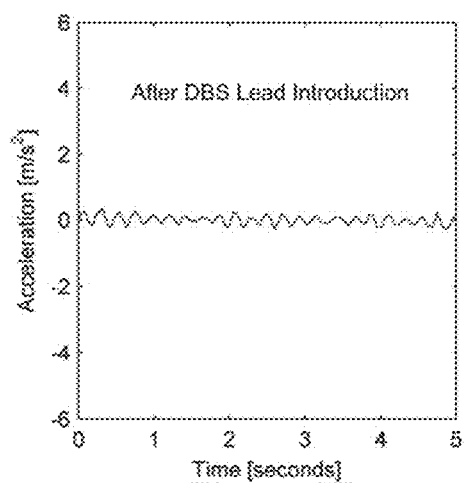

FIG. 9E shows a tremor acceleration plot after DBS lead introduction.

Figure 9F:
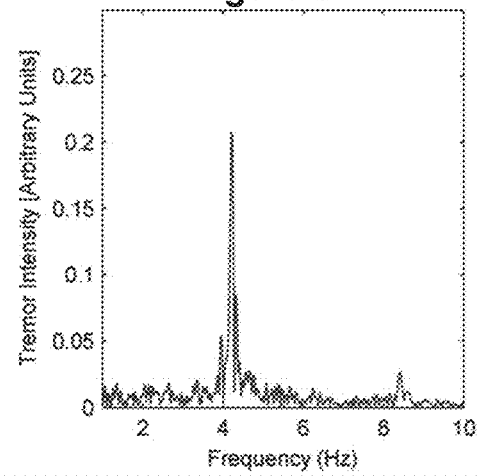

FIG. 9F shows a pre-operation tremor intensity plot.

Figure 9G:
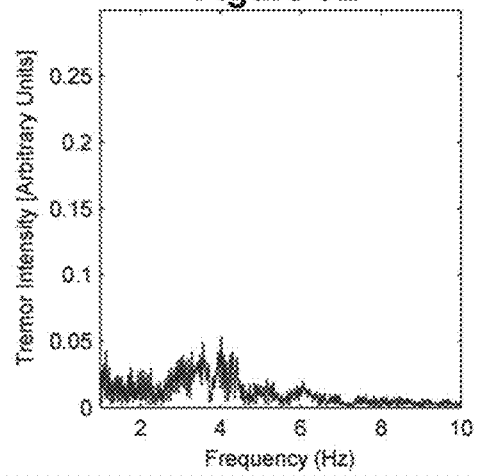

FIG. 9G shows a post-operation (after deep-brain stimulation lead introduction) tremor intensity plot.

Figure 10:
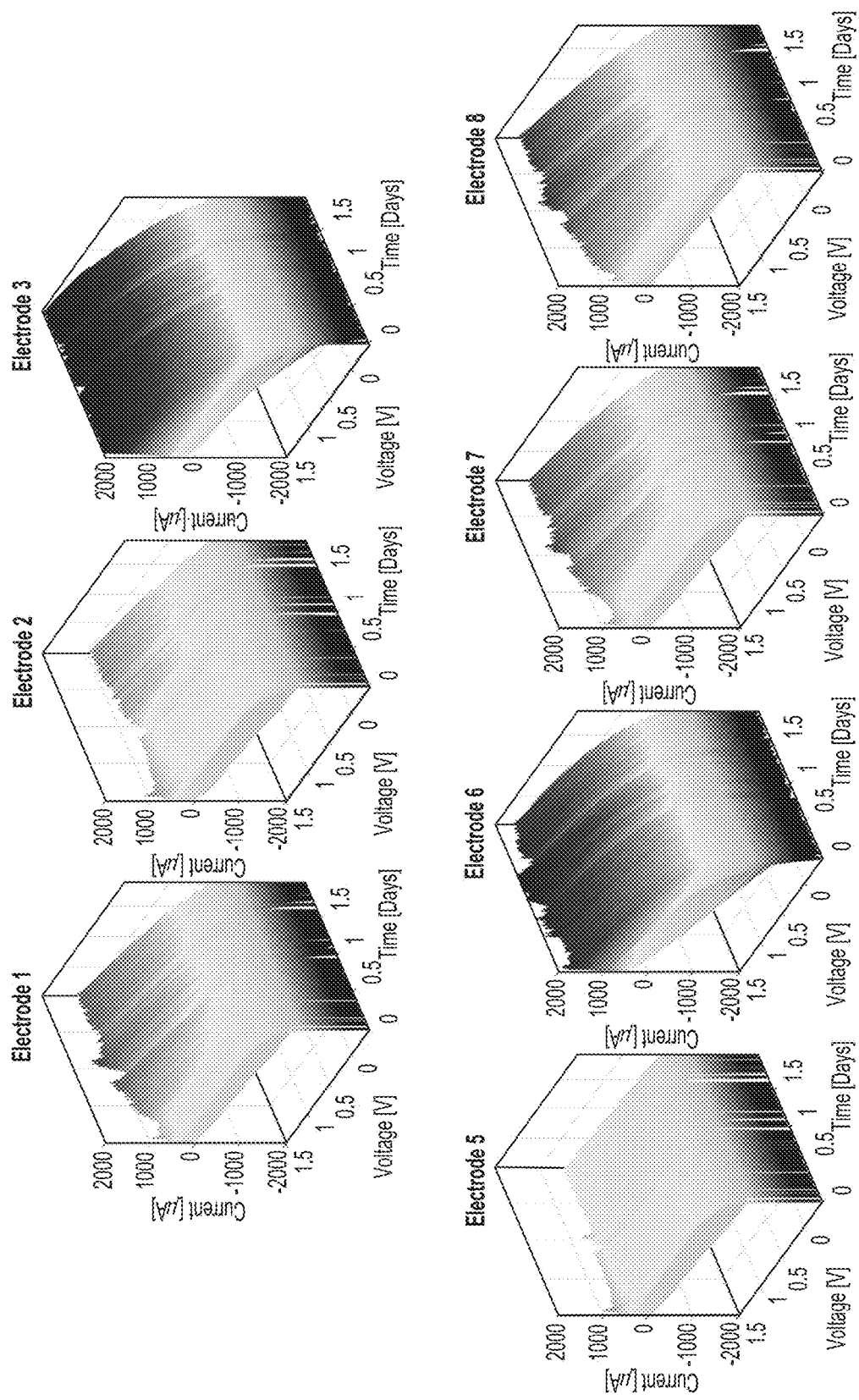

FIG. 10 shows cyclic voltammograms for a collection of carbon-fiber electrodes during an example study.

Figure 11:
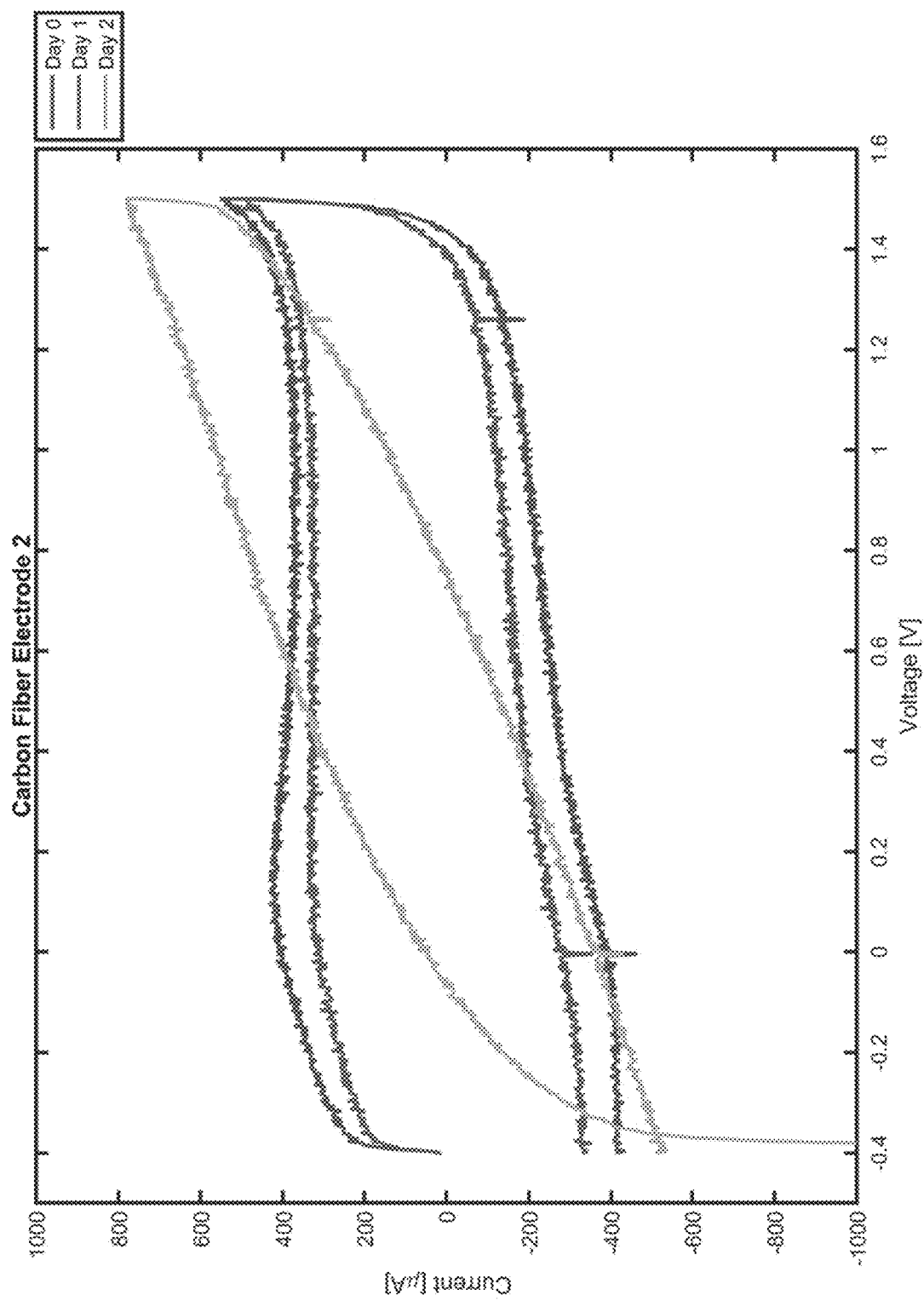

FIG. 11 shows plots of cyclic voltammograms for example carbon fiber electrodes for three days of a study period.

Figure 12:
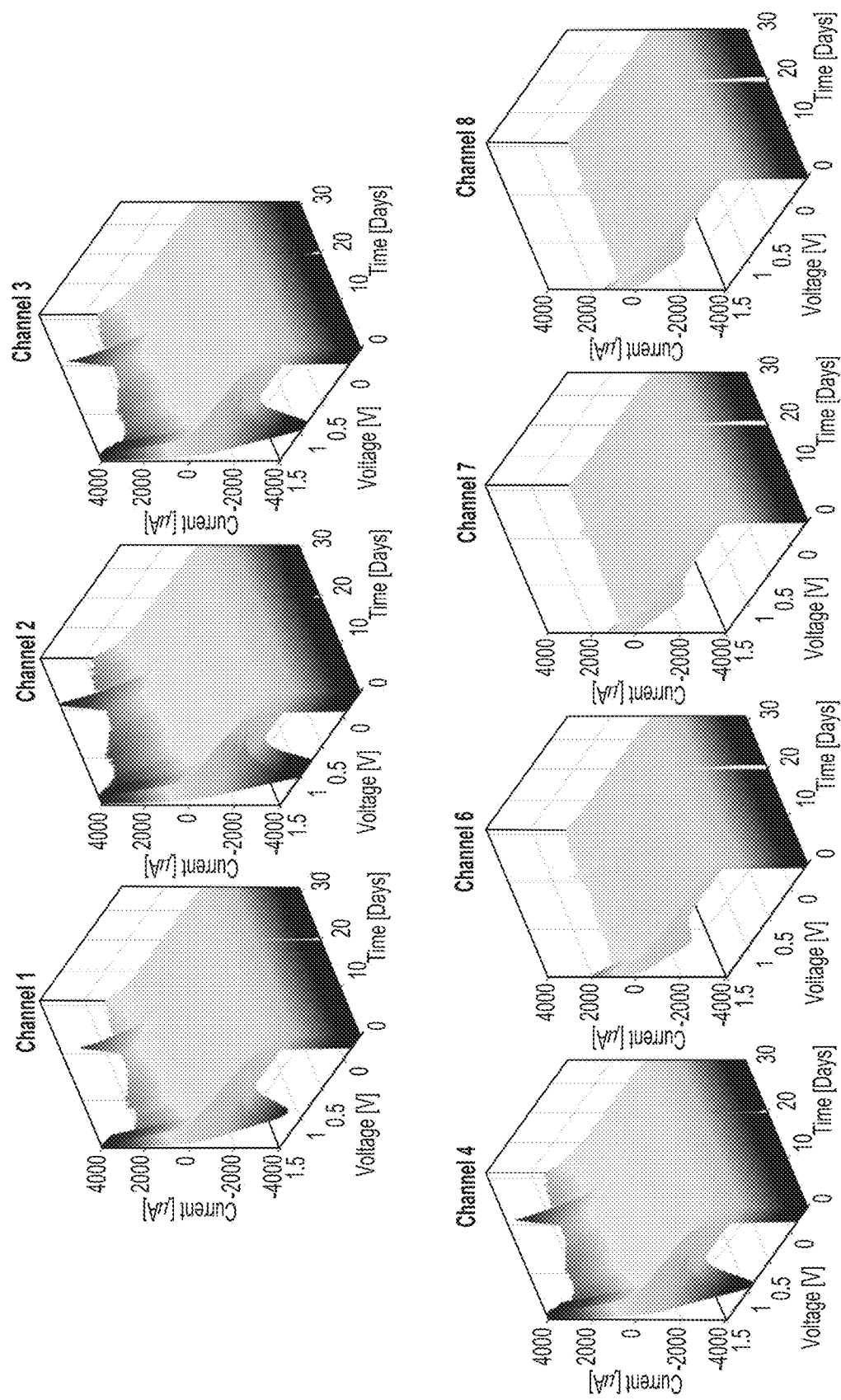

FIG. 12 shows cyclic voltammograms for a collection of boron-doped diamond-containing electrodes during an example study.

Figure 13:
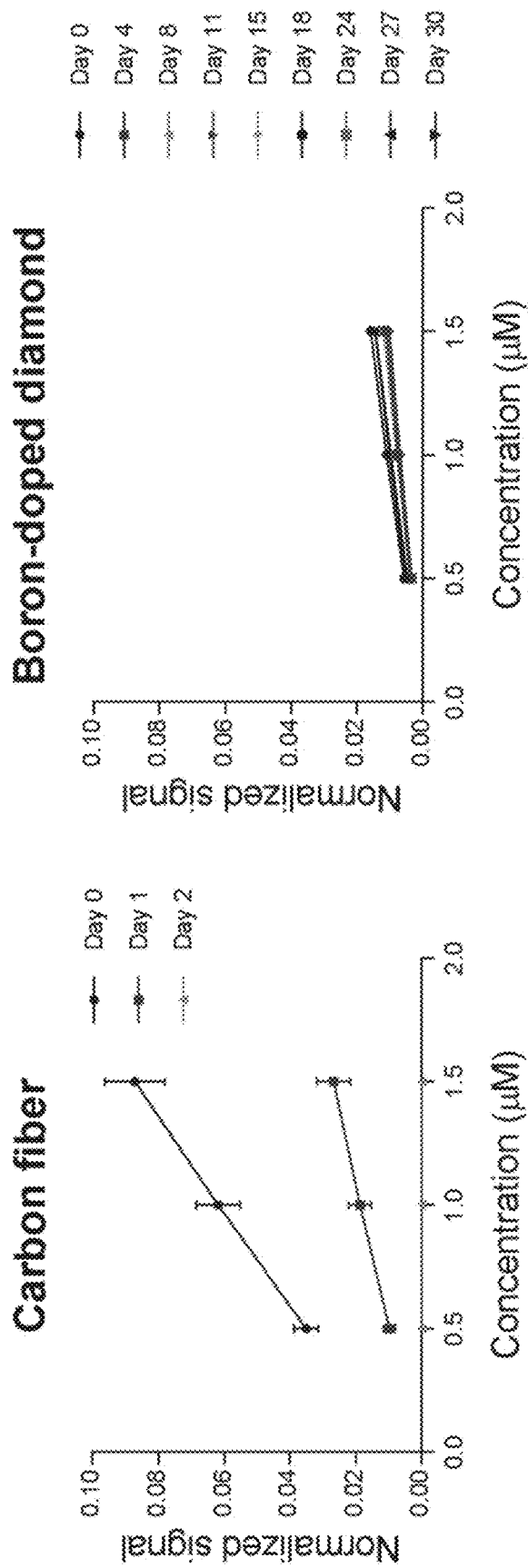

FIG. 13 shows plots representing changes to the cyclic voltammograms of boron-doped diamond containing electrodes over different days of a study period.

Figure 14:
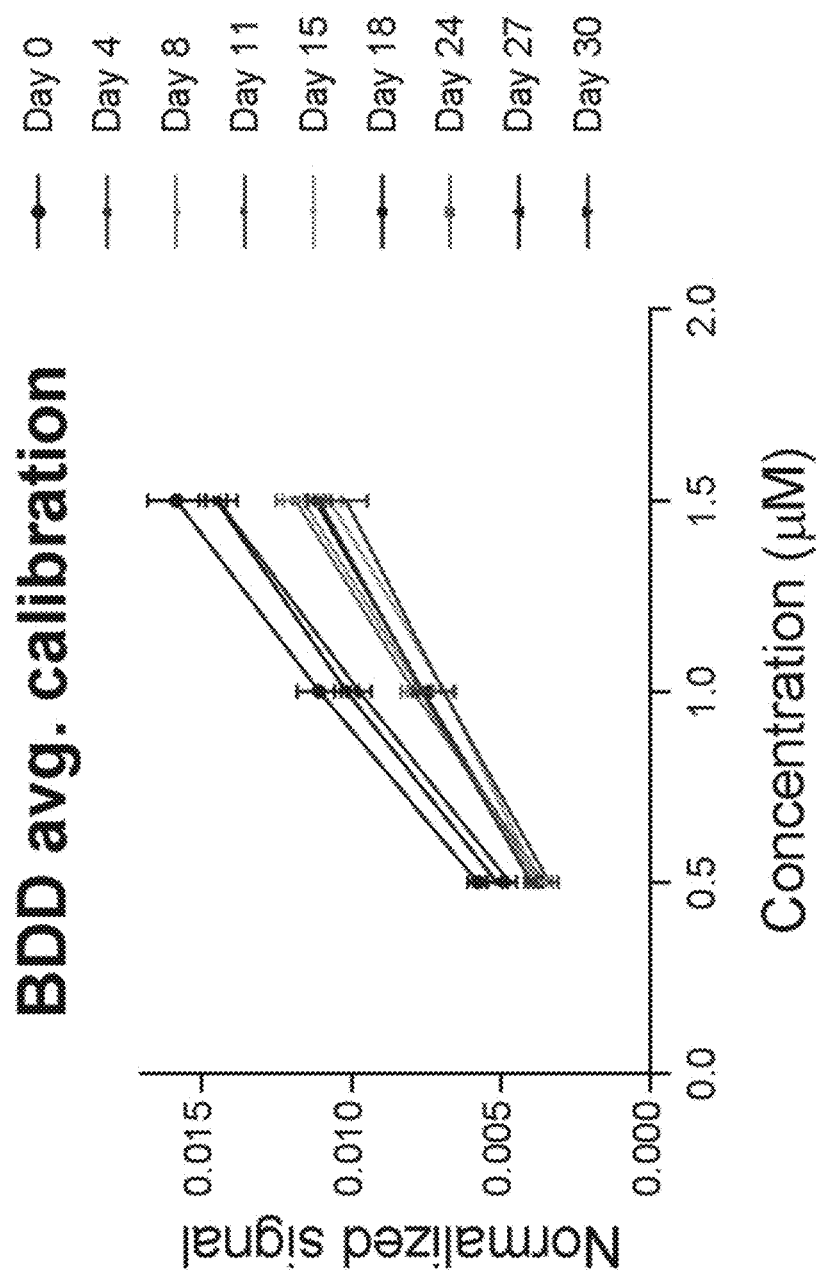

FIG. 14 is a plot showing the average calibration of boron-doped diamond electrodes at particular days during the course of a 30-day study.

Figure 15:
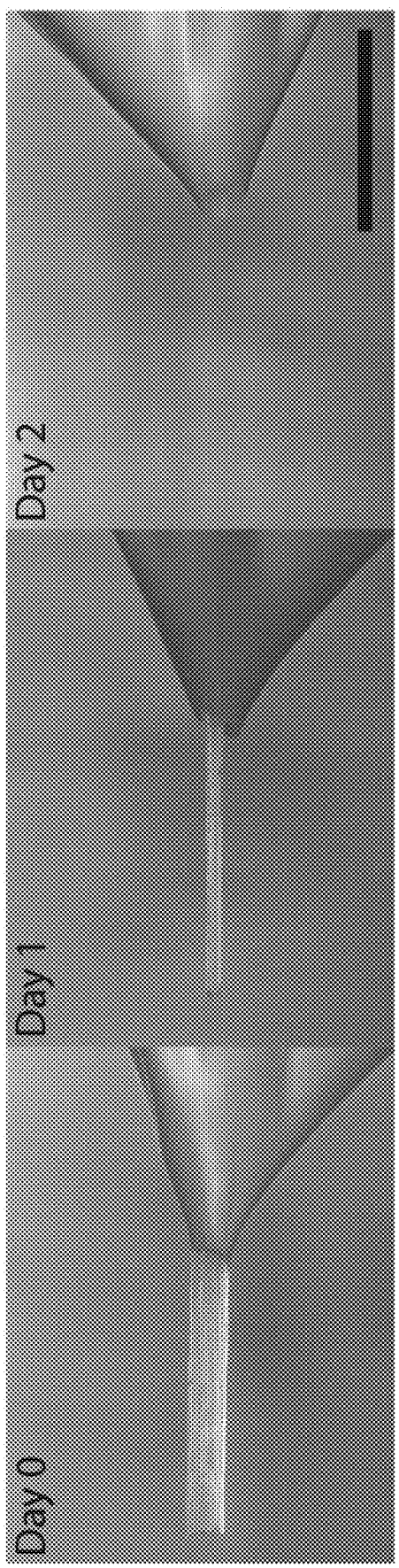

FIG. 15 shows images from scanning electron microscopy of a carbon-fiber electrode after the first three days of voltammetric cycling in solution during an example study.

FIG. 16A shows a first image from scanning electron microscopy of a boron-doped diamond-containing electrode before a voltmammetric cycling experiment.

FIG. 16B shows a second image from scanning electron microscopy of the electrode before the voltammetric cycling experiment.

FIG. 16C shows a first image from scanning electron microscopy of the electrode after the experiment.

FIG. 16D shows a second image from scanning electron microscopy of the electrode after the experiment.

DETAILED DESCRIPTION

This document provides methods and materials involved in making and using a diamond-containing electrode. For example, this document provides methods and materials for using voltammetry to discriminate analytes based on their adsorption characteristics to a diamond-containing electrode.

Stimulation-driven neurochemical release can be measured by fast-scan cyclic voltammetry (FSCV), but some FSCV electrodes rely on materials such as carbon fiber that degrade rapidly during use, thereby rendering these electrodes potentially problematic for chronic neurochemical recording. Accordingly, this document describes diamond-containing electrodes that, in some implementations, have been shown to provide significantly less degradation than carbon fiber electrodes in vitro. In some examples, a diamond-containing electrode may be employed for chronic neurochemical recording over much longer terms than can carbon fiber electrodes.

Some implementations of a diamond-containing electrode may include a synthetic boron-doped diamond material that coats a tungsten substrate. Films of polycrystalline boron-doped diamond can be deposited on conically-sharpened tungsten rods using a chemical vapor deposition process. Other suitable substrates may include silicon, gold, platinum, rhenium, or alloys thereof.

In some implementations, diamond-containing material in the electrode may include a mixture of $sp^3$-bonded carbon and $sp^2$-bonded carbon. Different types of diamond-containing material may be applied to an electrode configured for in vitro fast-scan cyclic voltammetry (FSCV), including varying compositions of $sp^3$-hybridized carbon and $sp^2$-hybridized carbon. The composition of the diamond variant can affect properties of the material, such as its hardness, flexibility, adsorption characteristics, surface finish (e.g., smoothness), lubricity, or a combination of these.

For example, diamond variants that may be suitable for the neurochemical detecting electrodes discussed herein can include between about 2-percent and about 30-percent $sp^2$-hybridized carbon or between about 2-percent and about 49-percent $sp^2$-hybridized carbon (e.g., from about 2-percent to about 5-percent, from about 2-percent to about 10-percent, from about 2-percent to about 15-percent, from about 2-percent to about 25-percent, from about 2-percent to about 30-percent, from about 5-percent to about 10-percent, from about 5-percent to about 20-percent, from about 5-percent to about 30-percent, from about 5-percent to about 40-percent, from about 10-percent to about 15-percent, from about 10-percent to about 25-percent, from about 10-percent to about 25-percent, from about 10-percent to about 35-percent, from about 20-percent to about 30-percent, or from about 20-percent to about 40-percent $sp^2$-hybridized carbon).

In some implementations, diamond variants that may be suitable for the neurochemical detecting electrodes discussed herein can include between about 50-percent and about 98-percent $sp^3$-hybridized carbon (e.g., from about 50-percent to about 55-percent, from about 50-percent to about 65-percent, from about 50-percent to about 75-percent, from about 60-percent to about 75-percent, from about 70-percent to about 85-percent, from about 85-percent to about 95-percent, from about 90-percent to about 98-percent $sp^3$-hybridized carbon). In some preferred examples, diamond-variants having from about 92-percent to about 98-percent $sp^3$-hybridized carbon and from about 2-percent to about 8-percent $sp^2$-hybridized carbon (e.g., about 95-percent $sp^3$ and about 5-percent $sp^2$, or about 97-percent $sp^3$ and about 3-percent $sp^2$) can be used in a diamond-containing electrode. In other implementations, a diamond-containing electrode may include substantially no $sp^2$-hybridized carbon and about 100-percent $sp^3$-hybridized carbon. In some implementations, a diamond-containing electrode may include about 96-100-percent $sp^3$-hybridized carbon.

In some implementations, in addition to having both $sp^3$- and $sp^2$-hybridized carbon, suitable diamond-containing material may further include other elements that affect various characteristics of the material. Depending upon application, diamond-containing material having a substantially pure mix of $sp^2$- and $sp^3$-hybridized carbon may provide sufficient conductivity. The diamond material may also be doped with a variety of materials such as graphene, carbon nanotubes, carbon nanofibers or materials such as boron, silicon, nitrogen, oxygen, fluorine or metals which, when combined, can modify physical and/or electrical properties, as well as resistance to oxidation, erosive attack or biological inertness of the material. For example, a diamond-variant containing from about 92-percent to about 98-percent $sp^3$-hybridized carbon and from about 2-percent to about 8-percent $sp^2$-hybridized carbon (e.g., about 95-percent $sp^3$ and about 5-percent $sp^2$, about 97-percent $sp^3$ and about 3-percent $sp^2$) may be doped with about 1-percent or less boron (e.g., about 0.3 percent) to increase the electrical conductivity of the diamond-containing material. The occurrence of $sp^3$-hybridized carbon (e.g., pure diamond), boron, and $sp^2$-hybridized carbon can be represented in a Raman spectrum for their characteristic Raman vibrations at 1332 $cm^{-1}$, centered around 550 $cm^{-1}$, and 1500 $cm^{-1}$, respectively.

In some implementations, a diamond-containing electrode can be made by depositing diamond-containing material over a conductive wire, e.g., a tungsten wire. The wire may then be electrochemically etched to create a sharpened tip, and all or a portion of the wire is coated, e.g., by chemical-vapor deposition, with the diamond-containing material. The wire can then be coated with parylene, e.g., by subjecting the diamond-coated wire to low pressure polymerization. In some examples, the parylene coating has a thickness in the range of about 20 μm to about 40 μm. In a preferred example, the parylene coating has a thickness of about 30 μm. The parylene coating provides an insulating coating along the shaft of the electrode and can enhance biocompatibility of the electrode. Other insulating materials may also be used as a coating over conductive substrate, including polyimide, ceramic (e.g., aluminum oxide), glass (e.g., quartz, silica), or a combination of these. Because the parylene or other insulating coating may initially coat the entire electrode, all or a portion of the electrode tip's diamond-containing layer may be exposed by selectively ablating the parylene coating, e.g., using a pulsed ultraviolet laser. For example, the first 100 μm of the electrode's tip may be ablated to expose the diamond-containing material. The portion of the tip having exposed diamond-containing material is preferably 100 μm, but may generally be in the range of about 75 μm to 125 μm. The thickness of the diamond-containing coating is preferably 1.5 μm, but may generally be in the range of about 0.2 to about 10 μm, in some examples.

In some implementations, a diamond-containing carbon electrode can be applied to perform FSCV for assessing a concentration of an analyte present within a tissue in vivo or in vitro. For example, the methods and materials provided herein can be used to assess the concentration of an analyte (e.g., a chemical such as a neurochemical or an ion) within brain tissue. In some cases, the methods and materials provided herein can be used to assess the concentration of an analyte during deep brain stimulation. Examples of analytes that can be detected using the methods and materials provided herein include, without limitation, ions such as calcium, magnesium, sodium, potassium, protons (pH), iron, copper, chromium, lead, mercury, cobolt, gold, lithium, cesium, barium, zinc, chloride, bicarbonate, phosphate, bromide, iodide, sulfide, oxide, sulfide, and fluoride and chemicals such as dopamine, serotonin, adenosine, adenine mono- or tri-phosphate, norepinephrine, GABA, histamine, acetylcholine, glutamate, aspartate, epinephrine, nitric oxide, glycine, trace amines (e.g., tryptamine, phenylethylamine, tyramine, and octopamine), and amino acid-based neuropeptides (e.g., endorphins, enkephalins, and vasopressin). For example, FSCV can be used to assess the concentration of one or more chemicals (e.g., dopamine or adenosine).

Figure 2A:
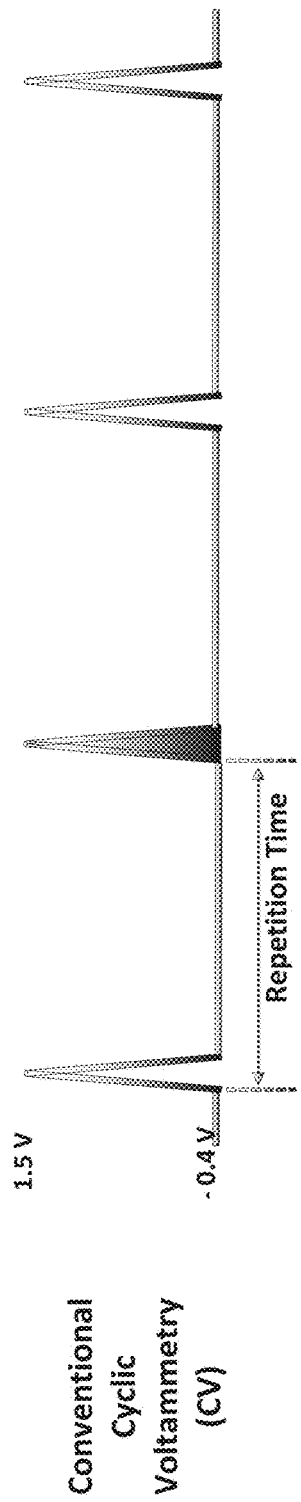
FIG. 2A is a diagram of a fast-scan cyclic voltammetry (FSCV) waveform.
Figure 2B:
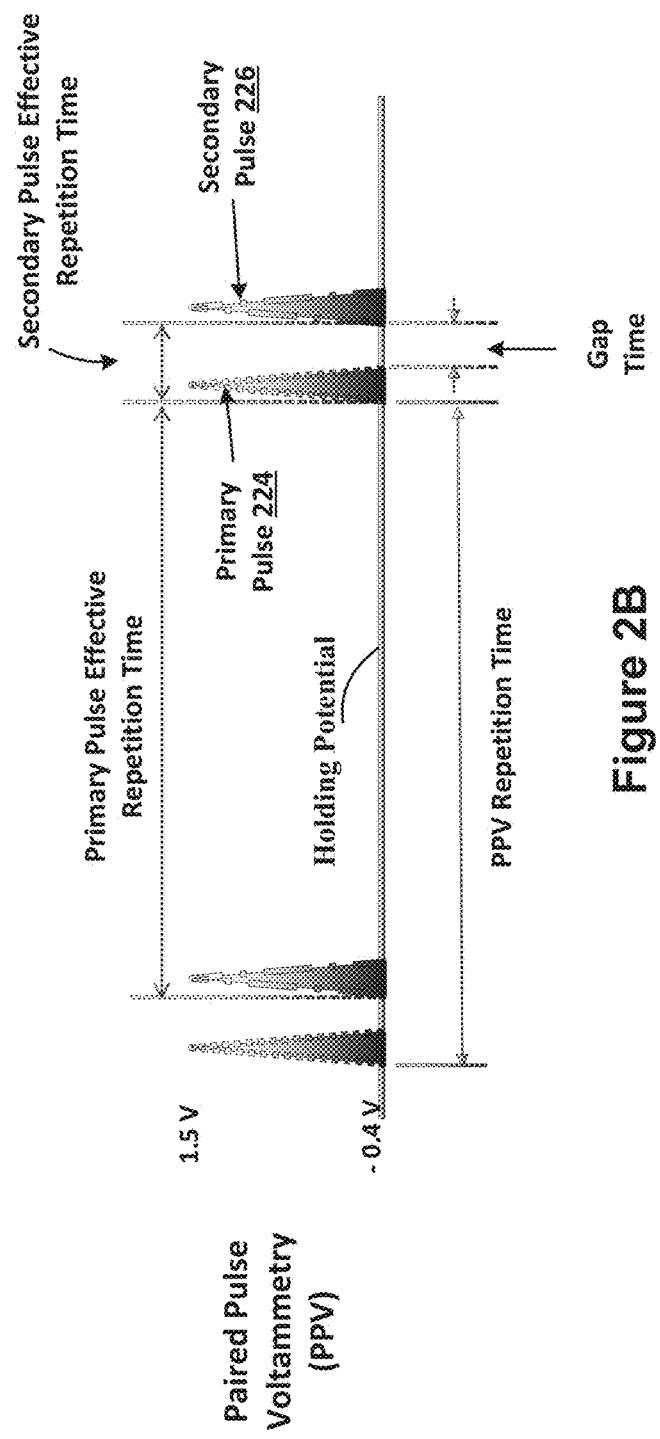
FIG. 2B is a diagram of an exemplary paired pulse voltammetry (PPV) waveform. This PPV waveform includes a selected binary waveform with a specific time gap between each of its two comprising pulses, such that each binary wave is repeated, while holding the working electrode at a constant potential between the waves. The primary pulse can have a long effective repetition time compared with the secondary pulse effective repetition time.

In some cases, the methods and materials provided herein can be used in a FSCV process to obtain voltammetric data for a primary pulse 224 and a secondary pulse 226 of a binary waveform (FIG. 2B). From this data, a primary voltammogram and a secondary voltammogram can be constructed. Once constructed, a difference between primary and secondary voltammograms indicative of the concentration of an analyte can be determined. For example, the secondary voltammogram can be subtracted from the primary voltammogram to create a difference voltammogram that provides an indication about the concentration of the analyte being assessed.

For example, a wireless instantaneous neurotransmitter concentration system (WINCS) device can be used to obtain voltammetric data pertaining to a tissue being assessed. In some cases, a voltammetry device can include one or more electrodes or sensors to detect one or more analytes. In some cases, a single electrode or sensor can be used to detect a single chemical. For example, a voltammetry device can include a first electrode designed to detect dopamine and a second electrode designed to detect glutamate. Another design uses a singular sensing electrode to detect different chemicals in quasi real time by applying different voltage ramps at slightly different times.

In some cases, a device (e.g., a WINCS device) can be implanted within a patient. For example, a WINCS device can be implanted within the thickness of a patient's skull. In some cases, a device can include a single electrode for FSCV that contains two independent areas of active electrode such as diamond-containing carbon. Then by varying the FSCV impressed voltage, signals representing different neurochemicals can be determined. If the active electrode areas are too close together, which would cause interference, the signals can be multiplexed such that the signal is detected quasi simultaneously by measuring one chemical directly after a preceding chemical. The device can also be used to determine the effect of stimulation. For example, stimulation of two different areas of the brain can produce a release of different neurochemicals (such as histamine, adenosine, glutamate, and dopamine). The ratio or absolute amount changes of the released neurochemicals can provide a physiologic effect of interest, such as creating long-term memory in patients with short-term memory loss.

In some cases, one or more chemicals (e.g., dopamine, adenosine, serotonin, and norepinephrine) can be detected using FSCV with various scan waveforms applied to one or more electrodes or sensors. The scan waveforms can be varied by manipulating physical aspects of the waveforms such as the peak voltage, voltage ramp, and repetition time.

When using PPV to assess the concentration of a particular analyte within a tissue in vivo, any appropriate PPV repetition time and any appropriate gap time of a binary waveform can be used (refer to FIG. 2B). For example, PPV repetition times ranging from about 30 milliseconds to about 1000 milliseconds (e.g., from about 30 milliseconds to about 750 milliseconds, from about 30 milliseconds to about 500 milliseconds, from about 30 milliseconds to about 250 milliseconds, from about 30 milliseconds to about 100 milliseconds, from about 40 milliseconds to about 1000 milliseconds, from about 50 milliseconds to about 1000 milliseconds, from about 100 milliseconds to about 1000 milliseconds, or from about 150 milliseconds to about 1000 milliseconds) and gap times ranging from about 1 millisecond to about 100 milliseconds (e.g., from about 1 millisecond to about 90 milliseconds, from about 1 millisecond to about 80 milliseconds, from about 1 millisecond to about 70 milliseconds, from about 2 millisecond to about 100 milliseconds, from about 3 millisecond to about 100 milliseconds, from about 5 millisecond to about 100 milliseconds, or from about 10 millisecond to about 100 milliseconds) can be used. Any appropriate form of pulse shape 224/226 can be used, such as a triangle shape pulse (FIG. 2B) or an N shape pulse.

One example of using paired pulse voltammetry (PPV) for differentiating analytes in a wireless instantaneous neurotransmitter concentration system (WINCS) using a carbon fiber microelecrode is described in paragraphs [0049]-[0072] and FIGS. 2-6 of U.S. Patent Application Publication No. 2013/0023745 to Lee et al, which is hereby incorporated by reference in its entirety.

Figure 1:
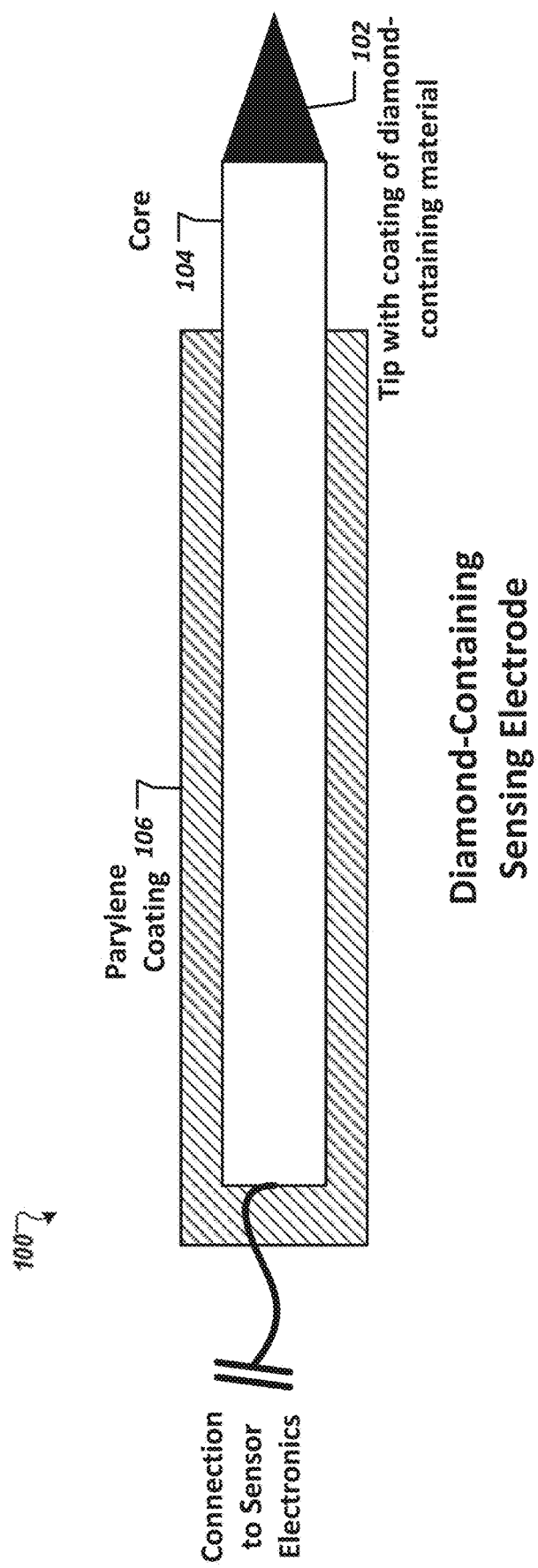
FIG. 1 depicts a conceptual diagram of an example electrode having a sensing tip made of diamond-containing carbon material. The electrode may be provided in a probe for deep brain stimulation or otherwise to detect analytes present in an environment.

Referring to FIG. 1, a conceptual diagram is shown of an example diamond-containing electrode 100 that may be employed as an electrical sensor for detecting concentrations of analytes in an environment. The electrode 100 is generally elongated and includes a tip 102 at a distal end that forms an active portion of the electrode 100 and is sensitive to the presence of analytes. Generally, the tip 102 is an adsorbent that adsorbs analytes at different rates depending on characteristics of the analyte, concentration of the analyte, and the applied voltage. The tip 102 generally extends from a core 104, which comprises a conductive material, and the core 106 may be coated along its length by an outer insulation layer or barrier 106 (e.g., parylene). At a proximal end of the electrode 100, conductors may extend to signal processing circuitry, which may include filters and amplifiers for capturing the electrical current response of the electrode 100 continuously, at select times, or on a periodic basis. In some implementations, such as in a WINCs device, the electrical current response of the electrode 100 may be detected, digitized, and transmitted wirelessly to a remote computer for further processing.

Other electrode constructions and geometries are also contemplated. For example, a block of diamond-containing material may be created or machined to form an electrode with a core of diamond-containing material, rather than, e.g., depositing the diamond-containing material over a conductive substrate. A variety of diamond geometries can be created, e.g., by machining a diamond block to the desired shape, including cube, cone cylinder, and tangent ogive. Machining may be accomplished using a femto second laser. An electrical connection can then be established between the diamond of the electrode to a WINCs device or other circuitry using cold weld pressure, sputtering, or evaporation.

Figure 3:
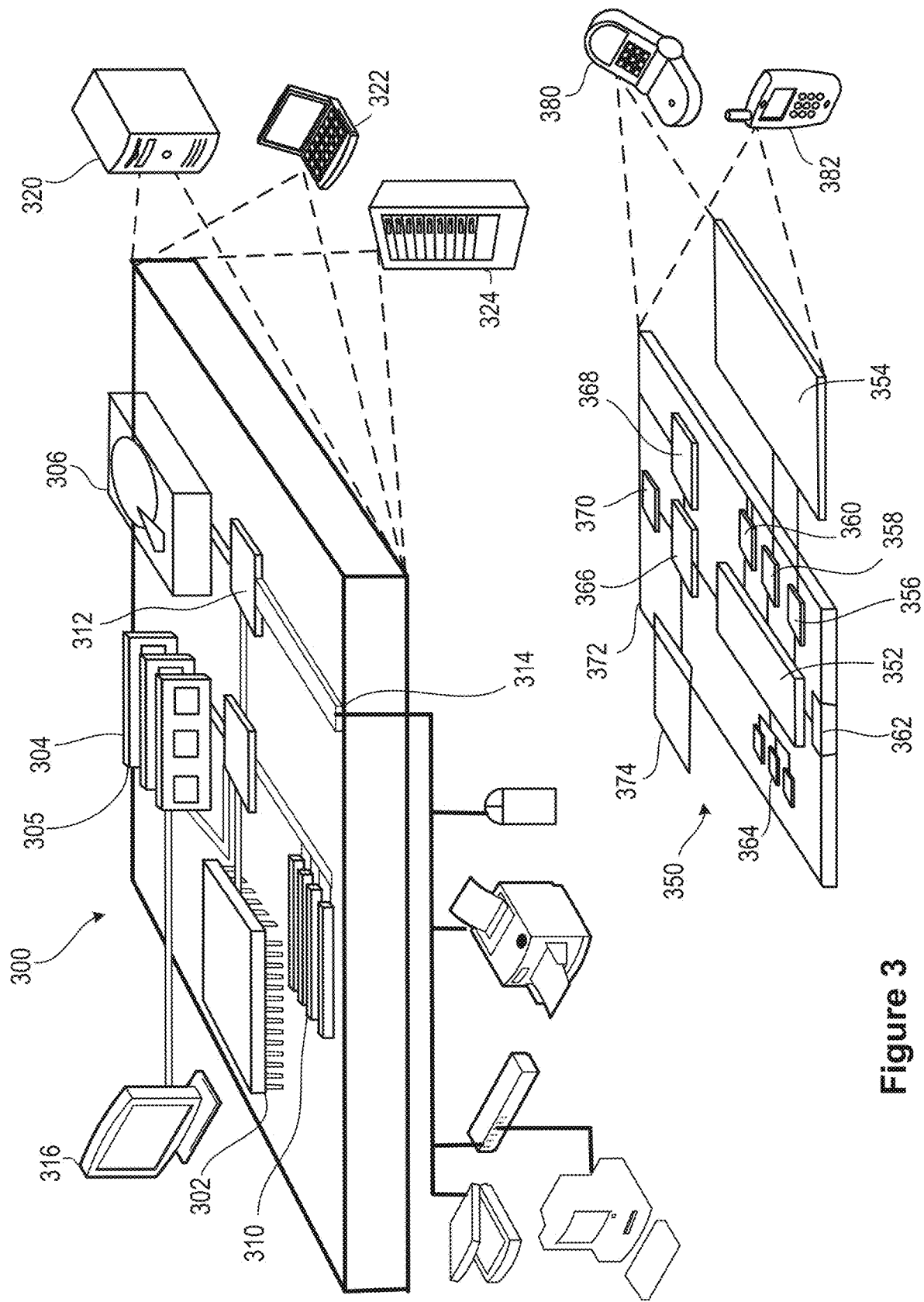
FIG. 3 is a block diagram of computing devices that may be used to implement the systems and methods described in this document, as one or more computers in one or more locations.

FIG. 3 is a block diagram of computing devices 300, 350 that may be used to implement the systems and methods described herein, as either a client or as a server or plurality of servers. Computing device 300 is intended to represent various forms of digital computers, such as laptops, desktops, workstations, personal digital assistants, servers, blade servers, mainframes, and other appropriate computers. Computing device 350 is intended to represent various forms of mobile devices, such as personal digital assistants, cellular telephones, smartphones, and other similar computing devices. The components shown here, their connections and relationships, and their functions, are meant to be exemplary only, and are not meant to limit implementations described and/or claimed in this document.

Computing device 300 includes a processor 302, memory 304, a storage device 306, a high-speed interface 308 connecting to memory 304 and high-speed expansion ports 310, and a low speed interface 312 connecting to low speed bus 314 and storage device 306. Each of the components 302, 304, 306, 308, 310, and 312, are interconnected using various buses, and may be mounted on a common motherboard or in other manners as appropriate. The processor 302 can process instructions for execution within the computing device 300, including instructions stored in the memory 304 or on the storage device 306 to display graphical information for a GUI on an external input/output device, such as display 316 coupled to high speed interface 308. In other implementations, multiple processors and/or multiple buses may be used, as appropriate, along with multiple memories and types of memory. Also, multiple computing devices 300 may be connected, with each device providing portions of the necessary operations (e.g., as a server bank, a group of blade servers, or a multi-processor system).

The memory 304 stores information within the computing device 300. In one implementation, the memory 304 is a volatile memory unit or units. In another implementation, the memory 304 is a non-volatile memory unit or units. The memory 304 may also be another form of computer-readable medium, such as a magnetic or optical disk.

The storage device 306 is capable of providing mass storage for the computing device 300. In one implementation, the storage device 306 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described herein. The information carrier is a computer- or machine-readable medium, such as the memory 304, the storage device 306, or memory on processor 302.

The high speed controller 308 manages bandwidth-intensive operations for the computing device 300, while the low speed controller 312 manages lower bandwidth-intensive operations. Such allocation of functions is exemplary only. In one implementation, the high-speed controller 308 is coupled to memory 304, display 316 (e.g., through a graphics processor or accelerator), and to high-speed expansion ports 310, which may accept various expansion cards (not shown). In the implementation, low-speed controller 312 is coupled to storage device 306 and low-speed expansion port 314. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 300 may be implemented in a number of different forms, as shown in the figure. For example, it may be implemented as a standard server 320, or multiple times in a group of such servers. It also may be implemented as part of a rack server system 324. In addition, it may be implemented in a personal computer such as a laptop computer 322. Alternatively, components from computing device 300 may be combined with other components in a mobile device (not shown), such as device 350. Each of such devices may contain one or more of computing device 300, 350, and an entire system may be made up of multiple computing devices 300, 350 communicating with each other.

Computing device 350 includes a processor 352, memory 364, an input/output device such as a display 354, a communication interface 366, and a transceiver 368, among other components. The device 350 may also be provided with a storage device, such as a microdrive or other device, to provide additional storage. Each of the components 350, 352, 364, 354, 366, and 368, are interconnected using various buses, and several of the components may be mounted on a common motherboard or in other manners as appropriate.

The processor 352 can execute instructions within the computing device 350, including instructions stored in the memory 364. The processor may be implemented as a chipset of chips that include separate and multiple analog and digital processors. Additionally, the processor may be implemented using any of a number of architectures. For example, the processor 410 may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 350, such as control of user interfaces, applications run by device 350, and wireless communication by device 350.

Processor 352 may communicate with a user through control interface 358 and display interface 356 coupled to a display 354. The display 354 may be, for example, a TFT (Thin-Film-Transistor Liquid Crystal Display) display or an OLED (Organic Light Emitting Diode) display, or other appropriate display technology. The display interface 356 may comprise appropriate circuitry for driving the display 354 to present graphical and other information to a user. The control interface 358 may receive commands from a user and convert them for submission to the processor 352. In addition, an external interface 362 may be provide in communication with processor 352, so as to enable near area communication of device 350 with other devices. External interface 362 may provide, for example, for wired communication in some implementations, or for wireless communication in other implementations, and multiple interfaces may also be used.

The memory 364 stores information within the computing device 350. The memory 364 can be implemented as one or more of a computer-readable medium or media, a volatile memory unit or units, or a non-volatile memory unit or units. Expansion memory 374 may also be provided and connected to device 350 through expansion interface 372, which may include, for example, a SIMM (Single In Line Memory Module) card interface. Such expansion memory 374 may provide extra storage space for device 350, or may also store applications or other information for device 350. Specifically, expansion memory 374 may include instructions to carry out or supplement the processes described above, and may include secure information also. Thus, for example, expansion memory 374 may be provide as a security module for device 350, and may be programmed with instructions that permit secure use of device 350. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described herein. The information carrier is a computer- or machine-readable medium, such as the memory 364, expansion memory 374, or memory on processor 352 that may be received, for example, over transceiver 368 or external interface 362.

Device 350 may communicate wirelessly through communication interface 366, which may include digital signal processing circuitry where necessary. Communication interface 366 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 368. In addition, short-range communication may occur, such as using a Bluetooth, WiFi, or other such transceiver (not shown).

Device 350 may also communicate audibly using audio codec 360, which may receive spoken information from a user and convert it to usable digital information. Audio codec 360 may likewise generate audible sound for a user, such as through a speaker, e.g., in a handset of device 350. Such sound may include sound from voice telephone calls, may include recorded sound (e.g., voice messages) and may also include sound generated by applications operating on device 350.

The computing device 350 may be implemented in a number of different forms, as shown in the figure. For example, it may be implemented as a cellular telephone 380. It may also be implemented as part of a smartphone 382, personal digital assistant, or other similar mobile device.

Additionally computing device 300 or 350 can include Universal Serial Bus (USB) flash drives. The USB flash drives may store operating systems and other applications. The USB flash drives can include input/output components, such as a wireless transmitter or USB connector that may be inserted into a USB port of another computing device.

Various implementations of the systems and techniques described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor. To provide for interaction with a user, the systems and techniques described herein can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described herein can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described herein), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

The invention will be further described in the following examples, which do not limit the scope of the invention described in the claims.

EXAMPLES

Example 1

In some aspects, boron-doped diamond-containing electrodes are capable of measuring neurochemical release in humans (e.g., in a deep-brain stimulation system). In the example described here, a study was conducted to determine the comparative performance of carbon fiber electrodes and diamond-containing electrodes that were made and used as described in the following paragraphs. In this study, diamond-containing electrodes were found to be more than two orders-of-magnitude more physically-robust and demonstrated longevity in vitro without deterioration. When applied in humans, diamond-containing electrode recordings from thalamic targets in four patients undergoing DBS for tremor produced signals consistent with adenosine release at a sensitivity comparable to carbon fiber electrodes.

Diamond-Containing Electrode Characterization.

The electrodes used in this study were prepared by depositing films of polycrystalline boron-doped diamond on conically-sharpened tungsten rods using chemical vapor deposition (CVD). Electrodes were prepared in batches of 8 to accommodate the size of the CVD reactor, and up to one batch per day was produced. The resulting boron-doped diamond-containing electrode tips were characterized by scanning electron microscope (SEM) (all batches) and Raman spectroscopy (select batches).

Imagery depicting an example electrode is illustrated in FIG. 4. The boron-doped diamond films were polycrystalline, with average crystal dimension within the range of 0.5-2 µm and a film thickness of approximately 5-10 µm. Both (1 1 1) and (1 1 0) orientations were observed. The diameter of the conical electrode tips was approximately 50 µm, and the exposed length around 100 µm for a total (geometric) surface area of approximately 10,000 µm$^2$. FIG. 4 provides more details of the electrode tip and parylene insulation layer/diamond film interface.

Figure 4E:
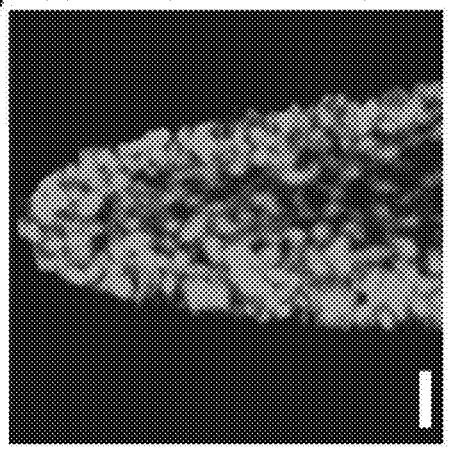
Figure 4D:
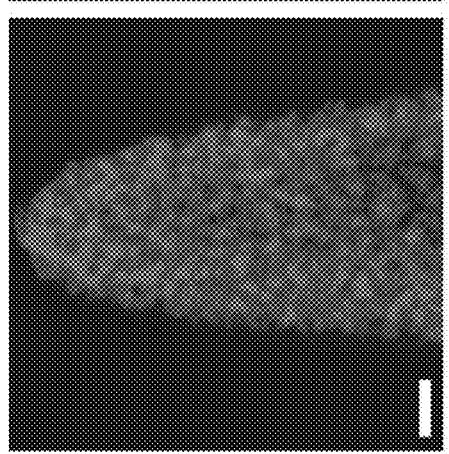

To allow visual determination of material constituents, Raman microscopy was performed at the electrode tip. The results are presented in FIGS. 4D and 4-E. The dominant magenta color resulting from a combination of blue (assigned to boron) and red (assigned to diamond) that is observed in FIG. 4D, demonstrates a relatively uniform incorporation of boron into diamond. As diamond is composed of carbon atoms exclusively bonded to each other by $sp^3$-hybridized orbitals, its characteristic Raman spectrum is a single peak at 1332 $cm^{-1}$. Besides the existence of this sharp peak, the integrated Raman spectrum of FIGS. 4D and 4E, presented in FIG. 4F, reveals other less intense bands. The broader band around 1500 $cm^{-1}$ is attributed to existence of carbon $sp^2$. The weak features around 1230 $cm^{-1}$ and 550 $cm^{-1}$ correlate with boron incorporation and accumulation in the diamond lattice, respectively (Bernard M, Baron C, Deneuville A. About the origin of the low wave number structures of the Raman spectra of heavily boron doped diamond films. Diam Relat Mater. 2004; 13(4-8):896-9). These data confirm that the crystal morphology observed in the SEM imagery does, indeed, correspond to boron-doped polycrystalline diamond.

Electrode Sensitivity and Longevity.

First, it is advantageous for a prospective FSCV electrode to produce a voltammogram with distinct signatures that correspond to analytes of interest (specificity). For instance, both dopamine and adenosine may be encountered in the thalamus—a common DBS target—and the electrode should be able to separate their signatures. Toward this end, dopamine, adenosine, and a combination of the two were presented to a diamond-containing electrode in a flow cell. As illustrated in FIG. 5, their oxidation and reduction signatures are quite distinct, and a combination of the two analytes produces a voltammogram that is a simple linear addition of the individual voltammograms.

While the in vivo data presented in this study are acute (no more than 30 minutes per patient were allowed by the IRB-approved experimental protocol), one benefit of diamond-containing electrodes (e.g., boron-doped diamond-containing electrodes) is improved longevity sufficient for chronic implantation. Two metrics that may be relevant to the construction of any electrode destined for chronic in vivo implantation are (i) sensitivity of the electrode to the analyte (s) of interest and (ii) the ability of the electrode to maintain that sensitivity after extended continuous use.

In this in vitro study, these metrics were tested by selecting dopamine as the test analyte, as the dopamine oxidation and reduction responses at CFMs using FSCV have been characterized elsewhere (Robinson D L, Venton B J, Heien M L, Wightman R M. Detecting subsecond dopamine release with fast-scan cyclic voltammetry in vivo. Clinical chemistry. 2003; 49(10):1763-73). Newly-fabricated diamond-containing electrodes were imaged with a scanning electron microscope and calibrated by subjecting them to dopamine in flowing Tris buffer while applying the FSCV voltage waveform. After calibration with dopamine, the electrodes were transferred to a bath of pure Tris buffer where the FSCV waveform was applied continuously for an extended period of time. CFMs (a current standard for FSCV use) were subjected to identical treatment as a control. After 72 and 144 hours of continuous use at these conditions, both types of electrodes were removed from the buffer and recalibrated. After the conclusion of the experiment, scanning electron micrographs were obtained. The results of the corresponding calibrations are depicted in FIG. 6.

Throughout the course of the experiment, the sensitivity decreased for both the diamond and the CFMs. The diamond film electrode average dopamine sensitivity (nA/µM) decreased 6.7% from t=0 to t=72 hrs (FIG. 6H; 95% confidence interval [CI]: −3.6% to 15.8%), and 16.1% from t=0 hrs to t=144 hrs (FIG. 6I; 95% CI: 7.8% to 23.4%). In contrast with the stability demonstrated by the diamond-containing electrode, the CFM's calibration curve revealed marked degradation in sensitivity after 24 hours. The CFM average dopamine sensitivity decreased 43.4% from t=0 to t=72 hrs (FIG. 3H; 95% CI: 37.5% to 48.9%) and 89.4% from t=0 hrs to t=144 hrs (FIG. 3I; 95% CI: 88.6% to 90.2%). After 144 hours of use—5.2 million measurement cycles—the CFM had become substantially insensitive to dopamine and the calibration experiment was discontinued, while the diamond-containing electrode retained 83.9% of its initial sensitivity.

After 3 and 6 (total) days of continuous use, both types of electrodes were subjected to imaging by SEM. The resulting SEM imagery is presented in FIG. 6(a-f). While the diamond-containing electrode showed no discernible changes, the CFM had been almost completely eroded. Given the chemical simplicity of the buffer solution, this erosion is most likely due to physical dissolution of the electrode tip by electrolysis reactions at the electrode surface, e.g., during the period of the FSCV waveform where the CFM is acting as the anode (positive polarity) with a voltage in excess of 1.2-1.4 volts:

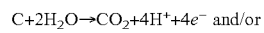

$$C+2H_2O \rightarrow CO_2+4H^++4e^- \text{ and/or}$$

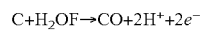

$$C+H_2OF \rightarrow CO+2H^++2e^-$$

While diamond is also an allotrope of carbon, the higher degree of covalent bonding may lead to the above reactions occurring at much slower rates.

Physical Robustness.

In some implementations, another relevant property of an electrode intended for human surgical use is its physical robustness with respect to mechanical damage. While electrochemical durability in a flow cell is a first step to a practical electrode design, the final electrode must resist forces stronger than those exerted by tissue resistance during implantation. The tissue of the living brain, while one of the softest tissues in the body, is still firm enough to break a single carbon fiber.

To quantify their relative resilience, both electrode designs were slowly forced into a stainless steel plate while the displacement distance and exerted force were simultaneously recorded. Both electrodes deformed by approximately 100-120 µm before failing; however the failure modes were very different. The CFM exerted a fairly constant force of about 0.1-0.15 gm against the plate as the carbon filament at the tip slowly bowed outwards. When the carbon fiber could bend no further, it snapped, and the force against the plate was reduced to zero.

The diamond-coated tungsten electrode tip, by comparison, did not break at any point. Rather, it slowly deformed as the sharp tip bent to one side and curled back on itself. Even after exerting 30-40 gm of force (approximately 200 times more force than caused the CFM to fail), the diamond-containing electrode remained largely intact. Both electrodes were examined by SEM following the test, and the only apparent damage to the diamond-containing electrode was some loss of the diamond coating where the bending of the tungsten substrate occurred. The carbon fiber electrode, by contrast, was destroyed.

Diamond-Containing Electrode Sensitivity In Vivo.

The results obtained regarding electrode longevity and strength suggest that, in some implementations, diamond-containing electrodes may be superior for chronic implantation as occurs for FSCV sensing in an implantable closed-loop DBS system. Following these in vitro trials of this example, a series of animal trials were conducted in both small (*Rattus norvegicus*) and large (*Sus scrofa*) animals to determine in vivo efficacy. However, to demonstrate the efficacy of diamond-containing electrodes for their intended application, volunteer test subjects were recruited from among patients undergoing DBS lead placement surgery for tremor disorders (Parkinson's disease and essential tremor).

In order to minimize risk to the patients, only one parallel surgical trajectory was permitted by the IRB-approved protocol, chosen based on the needs of the patients' intended DBS therapy. In patients selected for these studies, the therapeutic DBS lead—a standard 4-contact lead manufactured by MEDTRONIC (model 3387 or 3389)—was targeted at the VIM nucleus of the thalamus (n=3) or the STN (n=1). The diamond-containing electrode was inserted into the target region first, prior to the therapeutic DBS electrode, and mechanically-stimulated release of the neurochemical adenosine due to the "microthalamotomy" effect (Chang S Y, Kim I, Marsh M P, Jang D P, Hwang S C, Van Gompel J J, et al. Wireless fast-scan cyclic voltammetry to monitor adenosine in patients with essential tremor during deep brain stimulation. Mayo Clin Proc. 2012; 87(8):760-5. PMCID: 3538486) was observed, as depicted in FIG. 7. Although dopaminergic neurons have been shown to innervate parts of the non-human primate and human thalamus (principally dorsal aspects), only adenosine release was observed. This was likely due to the specific region of the thalamus targeted for DBS which has been shown to contain a relatively small number of dopaminergic terminals (Sanchez-Gonzalez M A, Garcia-Cabezas M A, Rico B, Cavada C. The primate thalamus is a key target for brain dopamine. J Neurosci. 2005; 25(26):6076-83).

In these experiments in humans (and in swine) an adenosine-like signature secondary to mechanical stimulation was observed, with oxidation peaks around 1.5V and 1.0V. The additional signature around 0.5V is most likely due to a local change in pH—a known effect in FSCV recordings using CFMs (Runnels P L, Joseph J D, Logman M J, Wightman R M. Effect of pH and surface functionalities on the cyclic voltammetric responses of carbon-fiber microelectrodes. Anal Chem. 1999; 71(14):2782-9). This represents an application of FSCV via diamond-based electrodes in human subjects and verifies the diamond-containing electrode's ability to sense evoked changes in the extracellular levels of neurochemicals in the human brain. Elsewhere, another series of experiments using CFMs in human subjects (Chang S Y, Kim I, Marsh M P, Jang D P, Hwang S C, Van Gompel J J, et al. Wireless fast-scan cyclic voltammetry to monitor adenosine in patients with essential tremor during deep brain stimulation. Mayo Clin Proc. 2012; 87(8):760-5. PMCID: 3538486) was performed. These experiments, conducted using the same protocol as the diamond experiments, also detected adenosine-like signatures secondary to mechanical stimulation, as depicted in FIG. 8.

FIG. 8(*c*) depicts mechanical stimulation of an adenosine-like species in the VIM of an awake human patient using a traditional CFM. This patient was undergoing DBS lead placement surgery for Parkinson's disease. FIG. 8(*d*) depicts an identical experiment (same target, same protocol) conducted in a different patient using a diamond-containing electrode. The biochemical milieu of the human brain is far more complex than the pure adenosine present in a flow cell. However, the signature oxidation peak at the potential of +1.5V is highly consistent with adenosine oxidation and was present in all cases. In the various panels of FIG. 8, it is clear that the diamond-containing electrode is less sensitive to the second oxidation peak of adenosine (around 1.0 V) than carbon fiber. The diamond-containing electrodes are also less sensitive to the broad feature associated with pH change located around 0.5 V. However, given that the relative strength of the various oxidation peaks for adenosine oxidation products can be variable even between different grades of carbon fiber (Swamy B E K, Venton B J. Subsecond detection of physiological adenosine concentrations using fast-scan cyclic voltammetry. Anal Chem. 2007; 79(2):744-50), the fact that there is some difference in behavior between carbon fiber and diamond—two entirely different carbon allotropes—is not surprising.

In some instances, human test subjects are useful in the sense that they are the ultimate intended environment for a chronic sensing electrode for a closed-loop DBS system, however human trials do present some unique challenges. Some challenges are involved in performing these tests with human test subjects, including the inability to pharmacologically-manipulate neurotransmitter levels, the short duration of recording that is possible, and a surgical trajectory that is defined and limited by the needs of the therapeutic procedure the patient is undergoing. All study patients were equipped with a hand-mounted wireless accelerometer. In the case of a representative patient depicted in FIG. 9 (essential tremor, lead placement in the VIM), the mechanically-evoked release of the neurochemical adenosine ("microthalamotomy effect") caused by lead placement was sufficient to produce an almost complete cessation in the patient's tremor. Prior to lead placement, this patient exhibited a strong tremor at 4.2 Hz as shown in FIGS. 9D and 9F, while this tremor is absent post-placement in FIGS. 9E and 9G.

This effect is common in human patients, even without an electrical current being applied to a stimulating electrode. The mechanical effect of lead placement alone is sufficient to ameliorate tremor. As depicted in FIGS. 7 and 8, mechanical advancement of the electrode is also associated with adenosine-like signals detectable by FSCV. While this link is not sufficient to draw conclusions vis-à-vis mechanism, it does demonstrate that the adenosine-like signals accessible to a diamond-containing electrode are related to the desired clinical outcome of tremor-reduction—a condition for closed-loop DBS.

Discussion.

A CVD diamond reactor has the ability to deposit films of high quality boron-doped polycrystalline diamond on tungsten electrode substrates. These diamond-coated tungsten needles can be employed to create durable and sensitive electrodes for FSCV.

After fabrication, these diamond-coated tungsten needles can form complete electrodes useful for electrochemical detection of neurochemicals. Furthermore, these diamond-containing electrodes, in conjunction with WINCS-based systems (Shon Y M, Chang S Y, Tye S J, Kimble C J, Bennet K E, Blaha C D, et al. Comonitoring of adenosine and dopamine using the Wireless Instantaneous Neurotransmitter Concentration System: proof of principle. J Neurosurg. 2010; 112(3):539-48. PMCID: 2852872) (Agnesi F, Tye S J, Bledsoe J M, Griessenauer C J, Kimble C J, Sieck G C, et al. Wireless Instantaneous Neurotransmitter Concentration System-based amperometric detection of dopamine, adenosine, and glutamate for intraoperative neurochemical monitoring. J Neurosurg. 2009; 111(4):701-11. PMCID: 2814519) (Bledsoe J M, Kimble C J, Covey D P, Blaha C D, Agnesi F, Mohseni P, et al. Development of the Wireless Instantaneous Neurotransmitter Concentration System for intraoperative neurochemical monitoring using fast-scan cyclic voltammetry. J Neurosurg. 2009; 111(4):712-23.

PMCID: 2808191), may be capable of detecting changes in extracellular concentrations of neurochemicals. Their ability to sense neurochemicals was verified with in vivo detection of adenosine-like signals in either the VIM nucleus of the thalamus or the STN of human patients undergoing D B S lead-placement surgery, comporting well with the findings of Chang et al. (Chang S Y, Kim I, Marsh M P, Jang D P, Hwang S C, Van Gompel J J, et al. Wireless fast-scan cyclic voltammetry to monitor adenosine in patients with essential tremor during deep brain stimulation. Mayo Clin Proc. 2012; 87(8):760-5. PMCID: 3538486).

This example study demonstrated that, at least in some implementations, the FSCV sensing lifetime of diamond-containing electrodes is greater than the lifetime of the current standard CFMs, showing little degradation over 5.2 million cycles (144 hours at 10 Hz), while a CFM was eroded and rendered almost substantially insensitive under the same conditions. If this was a chronic implant, 5.2 million scans would be roughly equivalent to 1 scan every 2 minutes for 20 years.

In addition, the diamond-containing electrode design exhibited a greater than 2 order-of-magnitude improvement in physical robustness with respect to mechanical damage of the tip.

Materials and Methods.

Chemicals were acquired from SIGMA-ALDRICH (St Louis, Mo.), and were used as received. All solutions were made using deionized (DI) water. Flow cell experiments were conducted in Tris buffer (150 mM sodium chloride and 12 mM Tris, pH adjusted to 7.4 with concentrated sodium hydroxide solution). For flow cell injection, 5 mM dopamine stock solution was prepared in DI water, and diluted to desired concentration in Tris buffer.

Both boron-doped diamond-containing and carbon fiber microelectrodes (CFMs) were utilized in the study discussed in this example. To prepare boron-doped diamond-containing microelectrodes, boron and carbon were co-deposited to form diamond films on tungsten wires (250 μm in diameter, A-M SYSTEMS, Carlsborg, Wash.) using custom developed, hot-filament chemical vapor deposition (CVD) techniques. The source gas was 1% methane in hydrogen with trimethylborane (1000 ppm in hydrogen) as the boron dopant source. The CVD reactor filament temperature was nominally maintained at 2000° C. and the total pressure at 20 torr. Prior to CVD processing, the tungsten wires were electrochemically etched in 1M sodium hydroxide by applying 10V AC voltage to create a tapered sharpened tip. The generated tungsten tips were sonicated with 100 nm diamond particles suspended in isopropyl alcohol. To obtain the diamond growth temperature, the tungsten substrates were positioned 8-10 mm from the hot filament.

After CVD boron-doped diamond deposition, the coated tungsten wires were subjected to low pressure polymerization, resulting in a ~30 μm coating of parylene-C. This material provided enhanced biocompatibility as well as providing an insulating coating along the shaft of the electrode. Since the parylene uniformly coats the entire electrode during deposition, the first ~100 μm of the electrode tip's boron-doped diamond coating is subsequently exposed by selectively ablating the parylene coating using a pulsed ultraviolet laser (PHOTOMACHINING, INC. of Pelham, N.H.). The electrode was inserted into an outer cannula (FHC, INC. Bowdoin, Me.) that served as a stainless steel reference electrode.

For comparison, a CFM was fabricated by attaching a single polyacrylonitrile-based carbon fiber (7 μm in diameter; CYTEC, Woodland Park, N.J.) to a Nitinol (an alloy of nickel and titanium) extension wire with a silver-based conductive adhesive. The connection between the carbon fiber and the Nitinol wire was covered with cured polyamic acid (polyamide). The exposed carbon fiber was trimmed under a dissecting microscope to a length of 50-100 μm. The details of CFM production, by way of example, are discussed by Chang et al. (Chang S Y, Jay T, Munoz J, Kim I, Lee K H. Wireless fast-scan cyclic voltammetry measurement of histamine using WINCS—a proof-of-principle study. Analyst. 2012; 137(9):2158-65. PMCID: 3360524).

Surface morphology and microstructure of the boron-doped diamond-containing electrode and CFM were imaged with a scanning electron microscope (HITACHI 54700 Field Emission SEM) under conditions of 1.0 kV accelerating voltage and 10 μA beam current.

The confocal Raman measurements were acquired using an ALPHA 300R WITEC system (Ulm, Germany) equipped with a UHTS300 spectrometer and a thermoelectrically cooled DV40-11 CCD detector. A frequency-doubled Nd:YAG laser at 532 nm was used for excitation. The samples were mounted on a piezoelectric, computer-controlled stage, with the film normal to the incident laser beam. To minimize the optical effects occurring from the inherent curvature of the tungsten rods, a NIKON 20× objective was employed.

The chemical morphology of diamond films was explored by 2-D surface confocal Raman mapping. To generate these Raman mapping images of 100 μm×100 μm dimensions, a Raman spectrum was recorded at every image pixel, for a total of more than 100,000 spectra. Mappings of material constituents, namely diamond, boron, and $sp^2$ type of carbon impurities, were first obtained using filters for their characteristic Raman vibrations at 1332 $cm^{-1}$, centered around 550 $cm^{-1}$, and 1500 $cm^{-1}$, respectively. The visual correlation of the spatial distribution of the above-mentioned constituents was accomplished by false coloring them with red (for diamond), blue (for boron), and green (for carbon impurities), and by merging these independent maps. To reduce the background noise, the intensity threshold for diamond, boron and non-diamond carbon peaks included in mapping was appropriately adjusted.

Fast-scan cyclic voltammetry (FSCV) detection of dopamine was achieved using wireless instantaneous neurochemical concentration sensing system (WINCS). Briefly, WINCS hardware incorporates front-end analog transimpedance amplifier circuitry, a BLUETOOTH transceiver and a microcontroller—all integrated with a multilayer printed wiring board (PWB). The microcontroller produces an FSCV waveform applied to the electrochemical sensors, digitizes the nanoampere level electrochemical signal after current-voltage conversion by the transimpedance amplifier and controls the flow of data to the base station. Digital telemetry between the remote WINCS unit and base station is achieved by an embedded BLUETOOTH transceiver. WINCS software, "WincsWare", (MAYO CLINIC, Division of Engineering) controls the scan parameters and operation of WINCS, such as starting and stopping data acquisition and transmission, modifying FSCV waveform, changing sampling rate, and nearly real-time saving, conditioning, and displaying transmitted data.

Both diamond and CFMs were calibrated with a custom designed flow cell. A FIALAB 3200 injection system (FI-ALAB INSTRUMENTS, Seattle, Wash.) was utilized to introduce Tris buffer and dopamine sequentially to the sensing electrode. Dopamine samples with concentration ranging from 0.5 μM to 10 μM were used for calibration and were prepared by diluting 5 mM stock solution in Tris buffer.

A triangular waveform was generated by WincsWare, with the potential ramped from −0.4 V to +1.5 V and back at a scan rate of 400 V/s. This waveform was continually applied to the electrode at 10 Hz. Ag/AgCl served as the reference electrode. For each dopamine sample, five injections were attempted. The cyclic voltammograms prior to and after each injection were collected and subtracted from each other to obtain the cyclic voltammogram of dopamine. The oxidation peak currents for those injections were then averaged for calibration.

To evaluate their long term durability, both diamond microelectrode and CFMs were continually subjected to the triangular waveform described above at 10 Hz for 144 hrs. Dopamine calibrations were taken prior to 72 hrs and after 144 hrs of waveform application.

Written informed consent was obtained from all patients prior to surgery. Under local anesthesia, an MM-compatible stereotactic head frame was fixed to the patient's head. A localizer box created nine fiducials as reference points to enable localization of MR images in stereotactic space. The patient was then transported to the MM scanner. MR imaging was conducted using a GENERAL ELECTRIC SIGMA 1.5 T MM clinical system operated by ECHOSPEED LX Version 9.1. The human DBS imaging protocol consists of MP-RAGE sequences using 1.5 mm slice thickness and 24 cm field of view. Using COMPASS navigational software, MM data were merged with the human Schaltenbrand and Wahren stereotactic atlas, and stereotactic coordinates for DBS electrode implantation were identified. The patient was then returned to the operating suite where, under local anesthesia, a skin incision in line with the trajectory coordinates was made followed by a 5-10 mm burr hole made in the skull using a high-speed drill. Microelectrodes for standard electrophysiological recording and for the FSCV recording using a sensing probe, called a "WincsTrode," were implanted simultaneously through 5-trajectory guide cannula system that was attached to the Alpha Omega microdrive system. As cellular activities were measured through the center trajectory to define the target, FSCV recordings were performed in a 2 mm anterior path from the center of the 5-trajectory guide cannula system. Once brain mapping was successfully performed, the electrophysiological recording electrode was replaced with the DBS electrode. Electrochemical recordings utilizing the WincsTrode were obtained to evaluate the concomitant changes in neurochemical extracellular levels.

To document potential microthalamotomy effects, the frequency and amplitude of hand tremor were recorded using a wireless accelerometer which was affixed to patients' wrists during surgery. To obtain a baseline, accelerometer recordings were made 20 seconds before DBS electrode implantation. During this DBS surgery in the operation room, FSCV recordings were performed using the WINCS system. There were no complications following DBS surgery and concurrent electrochemical recordings.

To perform FSCV recording, WINCS and WincsWare were utilized. For FSCV, the potential at the electrode was linearly scanned at 400 V/second in a triangular waveform from −0.4 V to 1.5 V and back to −0.4 V at 10 Hz for co-monitoring, when present, adenosine and dopamine. The electrode rests at a bias potential of −0.4 V between scans.

Prior to implantation in patients, effort were made to ensure safe and sterile implantation. WINCS units were sterilized by the STERRAD® hydrogen peroxide gas plasma process. Electrodes and accessory wires were sterilized with an ethylene oxide treatment. Ethylene oxide, the most common chemical sterilization method, is used for over 70% of all sterilizations and for 50% of all disposable medical devices. Ethylene oxide treatment was carried out for 24 hours at 60° C. with relative humidity above 30% and a gas concentration of 200 mg/l. This process was followed by a 72-hour decay period in which the sterilized electrodes were quarantined. Because the pre- and post-sterilization calibrations were nearly identical, it appeared that the ethylene oxide sterilization did not affect the structure and characteristics of either the diamond or carbon fiber-based FSCV electrodes.

Example 2

In this example, a study was conducted in which both carbon fiber electrodes (CF electrodes) and boron-doped diamond electrodes (e.g., diamond-containing electrodes) (BDD electrodes) were subjected to constant application of the FSCV waveform in a custom-designed longevity tester over the course of 30 days or until failure. Constant cycling of the waveform was only interrupted to measure the electrode sensitivity to dopamine injections with the Wireless Instantaneous Neurotransmitter Concentration Sensing (WINCS) system at regular intervals. Raman spectroscopic analysis was conducted on the BDD electrodes to study changes to the electrode constituency as a result of 30 days of constant application of the waveform. Cyclic voltammograms (CV) of CF electrodes collected during the study period revealed a significant change in the characteristic CV for carbon fiber after two days. Substantially complete degradation of the CF electrodes was confirmed with scanning electron microscopy (SEM). CVs of BDD electrodes initially indicated the presence of non-diamond carbon (NDC). After 20 days of constant FSCV, the NDC characteristics were no longer present in the CVs and the curves stabilized to a steady-state. SEM images reveal intact BDD crystal morphology with crystal boundaries that show preferential erosion due to constant FSCV.

CF electrodes were manually fabricated from 7 µm diameter carbon fiber (THORNEL T-300 PAN-Based Fiber, CYTEC ENGINEERED MATERIALS, Tempe, Ariz.). Briefly, fiber strands were separated and individually secured inside of fused silica capillary tubing (TSP020090, POLYMICRO-TECHNOLOGIES MOLEX, Phoenix, Ariz.) with amic acid (SIGMA-ALDRICH, St. Louis, Mo.) and cured at 190° C. for 1 h. The back end of the fiber was electrically connected to a 0.008 in. diameter nitinol wire (Small Parts with conductive paste consisting of a 1:1 v/v mixture of silver powder (STREM CHEMICALS, Inc. Newburyport, Mass.) and amic acid and cured to form polyimide. The nitinol wire and conductive paste joint was insulated with polyimide tubing and sealed with another bead of cured amic acid. Finally, the carbon fiber was cut to 50-100 µm with a razor blade.

BDD electrodes were fabricated in batches with a custom-made hot-filament chemical vapor deposition (HFCVD) reactor. Tungsten rods 0.01" in diameter (A-M Systems, Sequim, Wash.) were electrochemically etched in 2 M NaOH (VWR, Inc., Radnor, Pa.) to create conically tapered tips. The tungsten rods were sonicated first in a suspension of diamond nanoparticles (VENDOR) in isopropyl alcohol for 1 h to provide seed points for diamond nucleation in the HFCVD process and then in deionized water for 1 min. to rinse. Polycrystalline boron-doped diamond was grown onto the tungsten rods at 20 torr using a gas mixture of 89% hydrogen, 1% methane, and 10% trimethylborane (1000 ppm diluted in hydrogen) for 3 h at a substrate temperature of 800° C. This gas mixture resulted in a B/C ratio of 0.010 in the gas phase.

Following BDD growth, the electrodes were insulated with 25 μm of PARYLENE C (SCS COATINGS, Indianapolis, Ind.) and electrode sites were exposed with UV laser ablation (PHOTOMACHINING, INC., Pelham, N.H.).

Constant application of the FSCV waveform was performed by an Electrode Longevity Tester (ELT; submission detailing device and operation currently in progress). Designed specifically to interrogate the chronic behavior of FSCV electrodes, the ELT was used to apply an FSCV waveform of −0.4 to 1.5 V (vs. stainless steel) in a two-electrode EC cell at a scan rate of 200 V/s with the electrodes immersed in 1× phosphate-buffered saline (PBS) at 37° C. Electrodes were removed from the ELT regularly to determine electrode sensitivity to dopamine (DA). Seven electrodes of each material were tested. BDD electrodes were subjected to the FSCV waveform for 30 days, but the CF electrodes were removed from the ELT after 2 days owing to the dramatic change in the CV and loss of sensitivity.

DA sensitivity was measured in beaker with the Wireless Instantaneous Neurotransmitter Concentration Sensing (WINCS) system [S.-Y. Chang, I. Kim, M. P. Marsh, D. P. Jang, S.-C. Hwang, J. J. Van Gompel, S. J. Goerss, C. J. Kimble, K. E. Bennet, and P. A. Garris, "Wireless fast-scan cyclic voltammetry to monitor adenosine in patients with essential tremor during deep brain stimulation," in *Mayo Clinic Proceedings*, 2012, pp. 760-765; A. Kasasbeh, K. Lee, A. Bieber, K. Bennet, and S. Y. Chang, "Wireless Neurochemical Monitoring in Humans," *Stereotactic and Functional Neurosurgery*, vol. 91, pp. 141-147, 2013]. Also in a two-electrode setup, an FSCV waveform of −0.4 to 1.5 V (vs. Ag/AgCl) was applied at a scan rate of 400 V/s in room temperature 1×PBS. Background-subtracted oxidation current was measured for DA concentrations of 0.5, 1.0, and 1.5 μM, utilizing constant Na gas purging to prevent spontaneous oxidative degradation of the DA in solution.

The background-subtracted oxidation signal for each measurement was normalized to the background current in the CV at the oxidation potential according to the following equation:

$$\text{Normalized signal} = \frac{(i_{signal} - i_{background})}{i_{background}}$$

In this way, variations in signal strength due to differences in electrode area were accounted for.

The CVs of the electrodes as they were cycled in 1×PBS were recorded and plotted for the duration of the study period. For the CF electrodes, shown individually in three-dimensional plots in FIG. 10, the expected CV with the characteristic sp2 peak was initially observed. Within a day or two, the characteristic CV for CF was lost and replaced with a CV likely arising from fluid contact with the silver paste/nitinol joint. This transition is most evident in FIG. 10 for electrodes 1, 3, and 6-8, but is also present in electrodes 2 and 4, as shown in the representative CVs taken from CF electrode 2 at time points during Day 0, Day 1, and Day 2 (FIG. 11). As can be seen, the characteristic CV is clearly evident for Days 0 and 1, but is lost by Day 2.

The CVs of the BDD electrodes initially showed strong oxidation on the anodic sweep and subsequent reduction on the cathodic sweep, which is indicative of non-diamond carbon (NDC) [P. U. Arumugam, H. J. Zeng, S. Siddiqui, D. P. Covey, J. A. Carlisle, and P. A. Garris, "Characterization of ultrananocrystalline diamond microsensors for in vivo dopamine detection," *Applied Physics Letters*, vol. 102, June 2013; A. Medel, E. Bustos, L. M. Apatiga, and Y. Meas, "Surface activation of C-sp3 in boron-doped diamond electrode," *Electrocatalysis*, vol. 4, pp. 189-195, 2013; J. V. Macpherson, "A practical guide to using boron doped diamond in electrochemical research," *Physical Chemistry Chemical Physics*, vol. 17, pp. 2935-2949, 2015]. Over the course of the 30-day study period, those redox peaks gradually tapered away, resulting in a curve representative of conductive diamond (FIG. 12). By Day 20, changes to the CV reached a steady-state and demonstrated a very stable curve for the remainder of the study period (FIG. 13).

The CF electrodes produced a stronger signal to DA than the BDD electrodes for the first day of cycling, however the signal drastically dropped between Day 0 and Day 1 and was substantially lost by Day 2. In contrast, the sensitivity of the BDD electrodes remained relatively stable over the course of the entire 30-day study period (FIG. 14).

Scanning electron microscopy (SEM; MODEL, Hitachi, Japan) of the CF electrodes clearly showed electrode degradation within a single day of cycling. By the second day, the entire exposed electrode area had eroded, leaving a void in the insulation where the carbon fiber once had been. (FIG. 15)

SEM of the BDD electrodes before and after cycling revealed evidence of slight erosion at the crystal boundaries. However, the bulk crystal morphology and electrode shape remained largely unchanged. (FIG. 16)

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An electrode configured to sense neurochemicals present in brain tissue of a mammal using a fast-scan cyclic voltammetry technique, the electrode comprising a sensing portion having an outer surface, wherein the outer surface of the sensing portion comprises a diamond-containing material that includes a composition of both $sp^3$-hybridized carbon and $sp^2$-hybridized carbon, wherein a fraction of the $sp^3$-hybridized carbon in the diamond-containing material is greater than a fraction of the $sp^2$-hybridized carbon in the diamond-containing material.

2. The electrode of claim 1, wherein the composition of the diamond-containing material includes about 2-percent to about 8-percent $sp^2$-hybridized carbon, wherein the composition of the diamond-containing material includes about 92-percent to about 98-percent $sp^3$-hybridized carbon.

3. The electrode of claim 1, wherein the composition of the diamond-containing material includes about 2-percent to about 30-percent $sp^2$-hybridized carbon.

4. The electrode of claim 1, wherein the composition of the diamond-containing material includes about 50-percent to about 98-percent $sp^3$-hybridized carbon.

5. The electrode of claim 1, wherein the diamond-containing material of the outer surface of the sensing portion of the electrode is further doped with one or more material elements to increase electrical conductivity of the diamond-containing material.

6. The electrode of claim 5, wherein the one or more material elements includes boron.

7. The electrode of claim 1, wherein the diamond-containing material coats at least a portion of a conductive substrate.

8. The electrode of claim 1, wherein the conductive substrate comprises conductive material selected from the group consisting of tungsten, silicon, gold, platinum, and rhenium.

9. The electrode of claim 1, wherein a second portion of the electrode is coated in parylene, wherein the second portion is different from the sensing portion.

* * * * *